US006197587B1

(12) United States Patent
Guiltinan et al.

(10) Patent No.: US 6,197,587 B1
(45) Date of Patent: Mar. 6, 2001

(54) METHODS AND TISSUE CULTURE MEDIA FOR INDUCING SOMATIC EMBRYOGENESIS, AGROBACTERIUM-MEDICATED TRANSFORMATION AND EFFICIENT REGENERATION OF CACAO PLANTS

(75) Inventors: Mark J. Guiltinan, State College, PA (US); Zhijian Li, Tabares, FL (US); Abdoulaye Traore; Siela Maximova, both of State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/105,648

(22) Filed: Jun. 26, 1998

Related U.S. Application Data

(60) Provisional application No. 60/051,147, filed on Jun. 27, 1997, provisional application No. 60/069,704, filed on Dec. 16, 1997, and provisional application No. 60/051,133, filed on Jun. 27, 1997.

(51) Int. Cl.[7] ..................................................... C12N 5/00
(52) U.S. Cl. ......................... 435/410; 435/420; 435/430; 435/430.1
(58) Field of Search ................................. 435/410, 420, 435/430, 430.1, 431

(56) References Cited

U.S. PATENT DOCUMENTS

| | | |
|---|---|---|
| 4,204,366 | 5/1980 | Janick et al. . |
| 4,291,498 | 9/1981 | Janick et al. . |
| 4,301,619 | 11/1981 | Janick et al. . |
| 4,545,147 | 10/1985 | Janick et al. . |
| 5,304,725 * | 4/1994 | Nelson . |
| 5,312,801 | 5/1994 | Sondahl et al. . |
| 5,324,646 | 6/1994 | Buising et al. . |
| 5,530,182 | 6/1996 | Sondahl et al. . |
| 5,850,032 * | 12/1998 | Wann . |

OTHER PUBLICATIONS

Tahardi, J.S. et al., *Menara Perkebunan*, 63:(1):3–7, 1995.
Parfitt, A. et al., *Scientia Horticulturae*, 56:321–329, 1994.
Lopez–Baez, O. et al., *C.R. Acad. Sci. Paris*, 316:579–84, 1993.
Mallika et al., *J. Plantation Crops*, 20(2):114–122, Dec. 1992.
International Search Report dated Oct. 16, 1998.
Alemanno, L. et al., *Plant Cell, Tissue and Organ Culture*, 46:187–194, 1996.
Li, Z. et al., *In Vitro Cell. Dev. Biol.—Plant*, 34:293–299, Oct.–Dec., 1998.
Sondahl, M.R. et al., *Acta Horticulturae*, 336:245, 1993.
Pence, V.C. et al., *J. Amer. Soc. Hort. Sci.*, 104(2):145–148, 1979.
Alemanno, L. et al., *Plantations, recherche, developpemant*, Jul.–Aug., 1996, pp. 225–233.
Figueira, A. et al., *Somatic Embryogenesis in Woody Plants*, 2:291–310, 1995.

* cited by examiner

Primary Examiner—Leon B. Lankford, Jr.
(74) Attorney, Agent, or Firm—Thomas J. Monahan

(57) ABSTRACT

The present invention relates to improved methods of (i) inducing somatic embryogenesis from cacao tissue explants and (ii) regenerating cacao plants from somatic embryos. The invention further relates to cacao somatic embryos and plants obtained according to the methods of the invention. Novel tissue culture media adapted for use in the above-identified methods are also within the scope of the invention. The novel media of the invention include primary callus growth medium, secondary callus growth medium, embryo development medium, primary embryo conversion medium, secondary embryo conversion medium and plant regeneration medium.

16 Claims, 14 Drawing Sheets

RB,LB: RIGHT AND LEFT BORDER OF T-DNA
35S-p, 35S-t: CaMV35S PROMOTER AND TERMINATOR
SGFP: GREEN FLUORESCENT PROTEIN GENE
GUS: BELTA-GLUCURONIDASE GENE
NPTII: NEOMYSIN PHOSPHOTRANSFERASE GENE
tml3': TUMOR MORPHOLOGY LARGE GENE TERMINATOR

METHODS AND TISSUE CULTURE MEDIA FOR INDUCING SOMATIC EMBRYOGENESIS, AGROBACTERIUM-MEDICATED TRANSFORMATION AND EFFICIENT REGENERATION OF CACAO PLANTS

The present invention claims priority under 35 U.S.C. § 119 of provisional applications Ser. No. 60/051,147 filed Jun. 27, 1997; Ser. No. 60/069,704 filed Dec. 16, 1997; and Ser. No. 60/051,133 filed Jun. 27, 1997, the disclosures of which are hereby incorporated herein by reference.

FIELD OF THE INVENTION

The present invention relates to an improved method of inducing somatic embryogenesis and regenerating cacao plants from cacao tissue. The invention also relates to a method for transforming cacao using Agrobacterium-mediated transformation to introduce novel genetic material into cacao plant DNA and regenerating transgenic plants from transformed callus and somatic embryos. The invention further relates to novel culture media such as primary callus growth medium, secondary callus growth medium, embryo development medium, primary embryo conversion medium, secondary embryo conversion medium, and plant regeneration medium which media are adapted for use in the methods of the invention.

BACKGROUND OF THE INVENTION

Cacao (Thaeobroma cacao L.) is the second most important agricultural commodity in the international trade market for the tropical regions. Cacao powder and cacao butter, which are obtained from the processed cacao beans, are the most important ingredients in chocolate and confectionery products, and are also important additives in pharmaceutical and cosmetic products. Due to increasing demands for cacao-related products, there is an ever greater need for cacao trees with higher levels of productivity and improved cacao bean quality. Cacao trees have a high degree of genetic heterozygosity. A typical cacao planting contains a large population of trees grown from genetically different seeds, and relatively few trees produce exceptional yields, and about one third of the trees produce below average yields.

Since the majority of cacao commercially cultivated today is derived from a few varieties collected 50–60 years ago and has a narrow genetic base, cacao remains extremely vulnerable to diseases and other abiotic stresses. Up to 30% of the world cacao crop production is lost each year due to fungal and viral diseases and to attack by various insect pests (Wood and Lass 1987, Cocoa, 4th edition. Longman Sci & Tech and John Wiley & Sons, NY). In 1995, almost 50% of the total cacao bean production in Brazil was lost due to the witch's broom disease pathogen, and this raised concerns within the cacao industry, over the need for production of disease-resistant varieties. Continued improvement in cacao production, through the development and utilization of superior genotypes with desirable yield and bean quality characteristics, resistance to diseases and insect pests, and tolerance to drought and cold, via conventional breeding methods and biotechnology approaches, remains a great challenge. In this regard, the development of a reliable transformation system for cacao has become critical for the successful utilization of biotechnology for cacao tree improvement. Furthermore, it is desirable to be able to propagate vegetativelly higher-yielding trees to ensure uniform high yields.

During the past thirty years, attempts were made to use vegetative cloning of superior genotypes or selected trees produced through breeding as a means to increase the overall yield, quality, and agronomic performance of cacao. However, in spite of a great deal of effort over a number of years to devise improved methods for vegetative propagation, cacao trees are currently commercially reproduced only via cuttings. There are a number of disadvantages associated with the propagation of cacao plants via the rooting or grafting of plagiotropic cuttings. For example, this mode of propagation is expensive and labor intensive, propagation rates are low, there is a wide range of variation in the performance of individual cuttings, an undesirable bush-like growth pattern may occur, and there is a high degree of susceptibility to wind damage due to the lack of a taproot system. Thus, there is a great need in the art of cocoa cultivation for an efficient clonal propagation method that could provide plants agronomically similar to seed-derived plants.

Considerable effort was made to develop tissue culture-based propagation methods. However, cacao has proven to be notoriously recalcitrant to in vitro propagation (Flynn et al., (1990) Plant Tissue and Organ Cult. 20:111–117; Passey and Jones, (1983) J. Hort. Sci 58:589–592; Orchard et al., (1979) Physiol. Plant. 47:207–210).

Plant regeneration through somatic embryogenesis provides an alternative approach for clonal propagation of cacao. Somatic embryogenesis is the process by which somatic cells undergo bipolar development to give rise to whole plants by means of the development of adventitious embryos that occur without the fusion of gametes. Plants derived from somatic embryos are genetically identical to their parental donor cells, and have a taproot system and an orthotropic growth pattern similar to that of seed-derived plants.

Certain studies on somatic embryogenesis and plant regeneration of cacao have been performed. For example, Janick et al. (U.S. Pat. Nos. 4,204,366; 4,291,498; 4,301,619 and 4,545,147) and Sondahl et al. (U.S. Pat. No. 5,312,801) studied the possibility of inducing embryogenesis and regenerating plants of cacao.

Janick discloses a method for producing somatic embryos exclusively from immature zygotic embryo tissues of cacao using MS-based medium and increased (3-fold) $CO_2$ concentration. In that procedure, the conversion or germination of somatic embryos into seedlings or plantlets was problematic and mature plantlets were not obtained. (See, e.g. Wang and Janick, (1984) Hort. Sci. 19:839–841). Furthermore, as pointed out by the same inventors in a subsequent publication (Figueira and Janick, (1993) Acta Hortic. 336:231–236), somatic embryos derived from immature zygotic embryos have limited value for commercial propagation, because cacao seeds are produced mainly through open pollination and the zygotic embryos used as a starting material are untested genotypes, i.e., the zygotic tissues are not genetically identical.

Sondahl developed a method for inducing somatic embryogenesis and plant production which uses a non-zygotic somatic tissues obtained from mature cacao plants as a starting material. The Sondahl procedure uses an MS-based culture medium and high sugar content. The procedure involves the following steps: (i) inducing a friable embryogenic callus from non-somatic tissues in a callus induction medium; (ii) recovering immature embryos from the friable embryogenic callus in a liquid culture medium; (iii) producing first stage somatic embryos in a regeneration medium; (iv) developing second stage somatic embryos in a differentiation medium with a high osmotic potential (80–120 g/l sucrose); and (v) germination of mature somatic embryos in plant regeneration medium. Sondhal uses ABA and GA hormones for embryo induction. In this procedure, regeneration of cacao plantlets depends primarily on the secondary somatic embryos induced from primary embryos subjected to an extended culture period. Up to 8 different types of culture media, and multiple growth regulators such as cytokinins (including zeatin, kinetin, 6-BA and 2-iP), auxins (including NAA and IAA), gibberellic acid, and abscisic acid were required.

The development of a procedure for inducing somatic embryogenesis in non-zygotic tissues as described by Sondahl did not eliminate the problem associated with in vitro propagation of cacao. The procedure could not be applied to all somatic tissues of cacao. Only two types of tissue explants, nucellus (the inner layer of an ovule) and young flower bud petals, were responsive to the established culture conditions and were capable of producing somatic embryos. This is a significant disadvantage since nucellus tissue can only be obtained from young cacao fruits and the availability of young fruits is often limited. Cacao plants generally have a low number of fruits because the majority of young fruits tend to abort during development.

More importantly, the Sondahl procedure resulted in a very low frequency of somatic embryogenesis and plant regeneration. For example, according to examples cited in the patent description, only 8 cacao plants were successfully established in the soil from 30,160 cultured nucellus explants that generated a total of 948 primary somatic embryo, and only 7 plants were produced from 27,721 cultured petal explants that produced a total of 167 primary embryos (U.S. Pat. No. 5,312,801). Additionally, the Sondahl procedure was tested using only two cacao genotypes (EET-162 and UF-667). A recent study by a French group using the Sondhal method demonstrated that only 5 among 25 tested cacao genotypes were capable of producing somatic embryos, while the rest remained non-responsive (Lopez-Baez et al., (1993) CRAS, Paris 316:579–584). Thus, the utilization of the procedures known in the art has never been attempted commercially. The low frequency of embryogenesis and plant production and the inability to produce somatic embryos from the majority of cacao genotypes have precluded the practical use of the Janick and Sondahl methods. Accordingly, there remains a need in the art for the development of an efficient method for the regeneration of cacao plants.

Applicants have now developed effective procedures for the stimulation of somatic embryogenesis and plant regeneration from somatic tissues of cacao. The present procedure has significant advantages over the Janick and Sondhal procedures. The procedure of the present invention uses novel culture media that are not based on the MS basal medium. In fact, Applicants have shown that the MS medium is toxic to cacao cells, which may explain the low efficiency of the Janick and Sondhal procedures. Furthermore, the method of the invention does not require high $CO_2$ levels (as described by Janick) or high osmoticum (80–120 g/l sucrose as described by Sondhal). The embryo conversion medium of the invention is effective without high sucrose levels and without growth hormones. In contrast, the Sondhal procedure requires high osmoticum and hormones. Accordingly, Applicants have now surprisingly discovered a novel procedure and novel culture media that are more effective and simpler to use than those described by the prior art.

Genetic transformation of plant cells offers a unique method to modify the plant genetic milieu and thus expedite the introduction of valuable agronomic traits into existing genotypes. Two major approaches, biolistics (gene gun) and Agrobacterium tumefaciens-mediated gene transfer, have been developed for gene introduction in many plant species. The biolistics approach involves the introduction of DNA that is carried on metal particles which are accelerated by a high velocity force into target plant cells. Agrobacterium-mediated transformation is accomplished by utilizing the natural DNA delivery capabilities of the *A. tumefaciens* bacterium.

Over the years, attempts have been made by a number of research groups to develop workable transformation protocols for cacao using both of the above-mentioned methods. However, successful transformation of cacao using the biolistics approach has not been demonstrated. The reports of Purdy and Dickstein (Plant Disease 73: 638–639; 1989) and Sain et al. (Plant Cell Tiss Org Cult 37:243–251; 1994) provided the first evidence that a wild type *A. tumefaciens* strain is capable of transferring and integrating the T-DNA into the cacao genome. However, only non-regenerable tumorous callus tissue was obtained, and the use of non-tumorigenic strains of *A. tumefaciens* that had been modified to contain a disarmed Ti plasmid, failed to infect cacao cells.

Applicants have now developed a protocol for transformation of the somatic embryos and the production of transgenic cacao embryos and plants using non-tumorigenic strains of *A. tumefaciens*. Applicants are the first to obtain transformed cacao plants.

SUMMARY OF THE INVENTION

The present invention relates to an improved method of regenerating cacao plants by inducting somatic embryogenesis from cacao tissue explants and regeneration of cacao plants from somatic embryos using novel culture media. The culture media of the invention include primary callus growth medium, secondary callus growth medium, embryo development medium, primary embryo conversion medium, secondary embryo conversion medium and plant regeneration medium. The invention also relates to a method for transforming cacao tissues with *A. tumefaciens* and producing transgenic cacao plants.

Accordingly, in one aspect, the invention provides for a method of obtaining somatic embryos by culturing cacao tissue explants.

In another aspect, the invention relates to a method of regenerating cacao plantlets and mature cacao plants from cacao somatic embryos.

In yet another aspect, the invention relates to culture media (solid, semi-solid and liquid) adapted for induction of somatic embryogenesis and regeneration of cacao plants.

In yet another aspect, the invention relates to a method of inducing an Agrobacterium mediated transformation of cacao and regeneration of transgenic plants.

In a further aspect, the invention relates to somatic embryos and cacao plants obtained according to the methods of the present invention.

DETAILED DESCRIPTION OF THE INVENTION

Figure 1A:
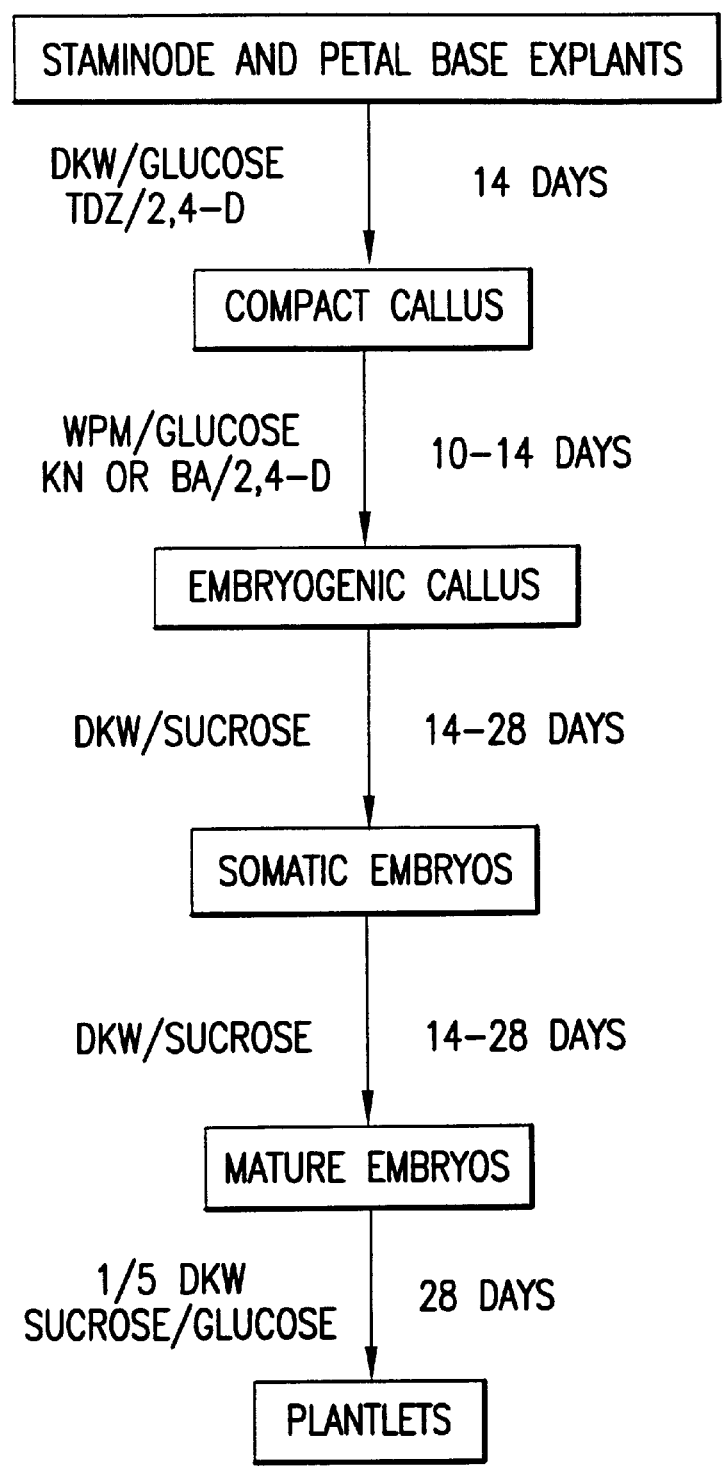
FIG. 1A represents a schematic outline of cacao plant regeneration in tissue culture according to one embodiment of the invention.

All patents, patent applications and publications cited herein are hereby incorporated by reference. In case of inconsistencies the present disclosure governs.

The present invention relates to improved methods of (i) inducing somatic embryogenesis from cacao tissue explants, (ii) regenerating cacao plants from somatic embryos and (iii) transforming cacao tissues and regenerating transgenic plants. The invention further relates to cacao somatic embryos and plants obtained according to the methods of the invention. Novel tissue culture media adapted for use in the above-identified methods are also within the scope of the invention. The novel media of the invention include primary callus growth medium, secondary callus growth medium, embryo development medium, primary embryo conversion medium, secondary embryo conversion medium and plant regeneration medium.

Method of Inducing Somatic Embryos

According to one embodiment of the invention, a method for inducing somatic embryos from cacao tissue explants is provided. The method generally includes the steps of obtaining cacao tissue explants, culturing explants to obtain callus and inducing somatic embryos in the callus.

Any cacao tissue may be used as a source of explants. For example, cotyledons from seeds, young leaf tissue, root tissues, parts of stems including nodal explants, and tissues from primary somatic embryos such as the root axis may be used. Generally, young tissues are a preferred source of cacao explants. In one preferred embodiment floral tissue explant, including staminodes (needlelike tissue fused with filament at the base of stamens) and petal base (cup-shaped pouch) are used. Cacao trees continuously produce flowers (year-round) and thus provide an unlimited source of floral explants. The advantage of the present invention is that it is effective on non-zygotic tissues. However, zygotic tissues may also be used.

Cacao explants are then placed on a primary callus growth medium to induce callus, which may be compact or friable. In one embodiment of the invention a rapidly growing compact callus is induced.

The "primary callus growth culture medium" (PCG) has the property of inducing callus growth and is a basal tissue culture medium characterized by a high content of the following ions: Ca, $SO_4$, Mg, $PO_4$, a low content of Cl and a higher ratio of $NO_3/NH_4$. For example, in one embodiment, PCG is characterized by a high content of calcium nitrate and potassium sulfate and a low content of calcium chloride and having the property of inducing callus growth. The meaning of the term "basal" is understood to mean a medium containing essential macro- and micronutrients. The meaning of the terms "high content" and "low content" is understood to be in reference to both Murashige and Skoog (MS) medium (Murashige and Skoog (1962) Physiol. Plant 15:473–497) and WPM medium. The MS medium has the following concentration of these ions (in mM): 43.4 $NO_3$; 21.0 NH4; 3 Ca; 1.6 $SO_4$; 1.5 Mg; 1.25 $PO_4$ and 3 Cl. Thus, the "high content" of the PCG medium for Ca ion, for example, is above 3 mM.

For example, the concentration of calcium nitrate may be from about 386.0 to about 2000.0 mg/l, preferably from about 800.0 to 1500.0 mg/l, most preferably about 1367.0 mg/l. The concentration of potassium sulfate may be from about 500.0 to about 2000.0 mg/l, preferably from about 990.0 to about 1800.0 mg/l, most preferably about 1559.0 mg/l. The concentration of calcium chloride may be from about 72.5 mg/l to about 150.0 mg/l, preferably from about 72.5 to about 112.5 mg/l, most preferably 112.5 mg/l. The primary growth medium may contain other components which may be in the ranges shown in Table 1.

TABLE 1

| | DKW (mg/l) | PCG (mg/l) |
|---|---|---|
| Ammonium Nitrate | 1416.0 | 400–2000 |
| Boric Acid | 4.8 | 0.3–10.6 |
| Calcium Chloride Anhydrous | 112.5 | 56–453 |
| Calcium Nitrate | 1367.0 | 386–2000 |
| Cupric Sulfate-5$H_2O$ | 0.25 | 0.006–0.5 |
| $Na_2$-EDTA | 45.4 | 10–75 |
| Ferrous Sulfate-7$H_2O$ | 33.8 | 13–50 |
| Magnesium Sulfate | 361.49 | 17–903 |
| Manganese Sulfate-$H_2O$ | 33.5 | 0.76–50 |
| Molybdic Acid (sodium salt)-2$H_2O$ | 0.39 | 0.0025–1.25 |
| Nickel Sulfate-6$H_2O$ | 0.005 | 0–0.01 |
| Potassium Phosphate Monobasic | 265.0 | 68–400 |
| Potassium Sulfate | 1559.0 | 500–2000 |
| Zinc Nitrate-6$H_2O$ | 17.0 | 5–30 |

Preferably, the primary callus growth medium comprises a DKW basal medium prepared according to Driver and Kuniyuki, Hortsci. 19:507–509 (1984). The composition of the DKW basal medium is shown in Table 1. DKW medium contains the following concentration of the ions (in mM): 34.3 $NO_3$; 17.7 $NH_4$; 8.3 Ca; 12 $SO_4$; 3 Mg; 1.9 $PO_4$ and 1 Cl.

The primary callus growth medium may be supplemented with at least two growth regulators such as, for example, a cytokinin, an auxin or a combination thereof. Preferably, thidiazuron (TDZ) is used but any cytokinin may be used. Most preferably, a combination of TDZ and 2,4 dichlorophenoxyacetic acid (2,4-D) are used. TDZ may be in the concentration of from about 0.1 μg/l to about 100 μg/l, preferably about 2.5 μg/l to about 50 μg/l, and most preferably from about 5 μg/l to about 10 μg/l. 2,4-D may be in the concentration from about 0.5 mg/l to about 5 mg/l, from about 0.8 mg/l to about 2 mg/l, and most preferably about 1.5 mg/l to about 2.0 mg/l.

The primary callus growth medium contains glucose or sucrose as a carbon source. Preferably, glucose is used. The concentration of the carbon source may be as generally used in the art and for example, from about 15 g/l to about 45 g/l, preferably about 20 g/l.

MS medium and McCown's WPM woody plant basal medium are not suitable for use as a basal media for the primary callus growth because the experiments have shown that they induce necrosis and reduce growth.

The explants are generally cultured on the primary callus growth medium for about 10 to about 30 days, and preferably about 14 days. The explants are cultured at temperatures generally known in the art as useful for callus growth, and for example, at 25±5° C.

The callus produced upon culturing cacao explants on primary callus growth medium is subcultured on a secondary callus growth medium. The "secondary callus growth medium" (SCG) is a basal culture medium characterized by a low salt concentration. The secondary callus growth medium has the property of "conditioning" the callus growth, i.e., limiting the callus growth and stimulating embryogenic homeostatic growth and bipolar callus cell development. Subculturing callus on SCG medium enhances subsequent embryo differentiation from callus cells. The elimination of this subculture step may result in excessive callus proliferation and a dramatic reduction in the frequency of somatic embryogenesis.

The secondary callus growth medium may contain from about 50% to about 25% salt concentration of culture media generally known in the art. Any media known in the art (e.g. DKW, MS) diluted as described above may be used. Preferably, a low salt WPM basal medium described by Lloyd and McCown, Int. Plant Prog. Soc. Proc. 30:421–427 (1981) may be used. The components and concentration of WPM medium as well as the ranges of compounds that may be used are shown in Table 2.

TABLE 2

| | WPM (mg/l) | SCG (mg/l) |
|---|---|---|
| Ammonium Nitrate | 400.0 | 400–2000 |
| Boric Acid | 6.2 | 0.3–10.6 |
| Calcium Chloride Anhydrous | 72.5 | 56–453 |
| Calcium Nitrate | 386.0 | 386–2000 |
| Cupric Sulfate-5$H_2O$ | 0.25 | 0.006–0.5 |
| $Na_2$-EDTA | 37.3 | 10–75 |
| Ferrous Sulfate-7$H_2O$ | 27.8 | 13–55 |
| Magnesium Sulfate | 180.7 | 17–903 |
| Manganese Sulfate-$H_2O$ | 22.3 | 0.76–33 |
| Molybdic Acid (sodium salt)-2$H_2O$ | 0.25 | 0.0025–1.25 |
| Potassium Phosphate Monobasic | 170.0 | 68–400 |
| Potassium Sulfate | 990.0 | 500–2000 |
| Zinc Sulfate-7$H_2O$ | 8.6 | 0.2–43 |

The secondary callus growth medium is supplemented with at least one growth regulator. At least one cytokinin, such as for example kinetin or 6-benzyl adenine (6-BA), and in some embodiments at least one auxin, such as for example, 2,4-D may be used. Kinetin may be used in the concentration of from about 0.01 mg/l to about 1 mg/l, preferably about 0.1 mg/l to about 0.5 mg/l, and most preferably from about 0.2 mg/l to about 0.3 mg/l. 6-BA may be used in the concentration from about 0.01 mg/l to about 1 mg/l, from about 0.05 mg/l to about 1 mg/l, and most preferably from about 0.05 mg/l to about 0.2 mg/l. 2,4-D may be used in concentration from 0.9 to 3 mg/l, most preferably from 0.9 to 2.0 mg/l.

In one embodiment, the secondary callus culture medium may contain a combination of coconut water (in the place of 6-BA) and kinetin as growth regulators. Kinetin may be used in the concentrations described above, while coconut water may be used in the concentration from about 25.0 to about 200.0 ml/l, preferably from about 25.0 to about 150.0 ml/l and most preferably from about 50.0 to 100.0 ml/l.

TDZ is not used in the secondary callus culture medium.

The secondary callus growth medium contains glucose or sucrose as a carbon source. Preferably, glucose is used. The concentration of the carbon source may be as generally used in the art and for example, from about 10 to 40 g/l, preferably from 20 to 30 g/l.

The callus is generally cultured on the secondary callus growth medium for about 10 to about 30 days, and preferably about 14 days at temperatures generally known in the art and for example 25±5° C.

The callus conditioned on the secondary callus growth medium is then transferred onto the embryo development medium which has the property of inducing formation of differentiated embryos. The "embryo development medium" is a basal culture medium having the same composition as the basal medium of the primary callus growth medium. For example, the basal medium may be DKW basal medium. However, the embryo development medium is not supplemented with growth hormones. The medium contains a carbon source and may contain sucrose from about 10 to 60 g/l, preferably about 30 g/l.

The embryogenic callus is generally cultured on the embryo development medium for about 14 to about 60 days, and preferably about 30 days. During this period, a number of mature somatic embryos are visible in the callus. These embryos may then be used to regenerate cacao plants or as a source of cacao tissue for production of secondary embryos by following the procedure outlined above.

The above described steps of the method for inducing somatic embryos in cacao explants may be carried out in the dark or under the light. Preferably, the steps are carried out in the dark.

Method of Regenerating Cacao Plantlets

The present invention further relates to a method for regenerating cacao plantlets and mature plants from cacao somatic embryos. The procedure generally includes the steps of (i) germinating embryos and (ii) inducing the growth of cacao plantlets.

Somatic embryos may be germinated on a primary embryo conversion medium. The "primary embryo conversion medium" contains the basal medium as described for the basal medium of the primary callus growth medium (e.g. DKW medium), and is fortified with $KNO_3$ in the concentration from about 0.1 g/l to 1.0 g/l, and preferably about 0.3 g/l. The medium also contains glucose or sucrose as a carbon source. The concentration of the carbon source may be as generally used in the art, such as for example from about 5 g/l to about 30 g/l. The somatic embryos are germinated under light for a period of about 10 to about 30 days at temperatures known in the art and for example at 25±5° C.

To achieve regeneration of whole cacao plantlets, germinating embryos are transferred onto a secondary embryo conversion medium. The "secondary embryo conversion medium" contains a diluted basal medium supplemented with a source of potassium and nitrogen, such as for example, $KNO_3$ and a carbon source which may be glucose, sucrose or a combination thereof. The "basal" medium may be as described for the primary callus growth medium, but other media known in the art such as MS medium may be used. The choice of the basal medium is not critical in this step. However, the basal medium is "diluted," to facilitate the autotrophic development of germinating embryo-derived plantlets. Various dilutions of known media may be used and determining the most useful one is a matter of optimization. For example a 1:2 to 1:10 dilution may be used.

The source of potassium and nitrogen can be any compound or a combination of compounds that provide K and $NO_3$ ions. Preferably, $KNO_3$ is used.

The carbon source may be used in the concentration generally known in the art. For example, when a combination of glucose and sucrose is used, glucose is in the amount from about 1 g/l to about 20 g/l and sucrose is in the amount from about 1 g/l to about 10 g/l. If glucose alone is used, the amount is from about 1 g/l to about 20 g/l. If sucrose alone is used, the amount is from about 5 g/l to about 40 g/l.

According to one embodiment of the invention, the steps of germinating embryos and regenerating cacao plantlet described above may be performed in a single step by transferring somatic embryos to a plant regeneration medium and culturing the embryos until plantlets are formed. The "plant regeneration medium" contains a diluted basal medium as described above for the secondary conversion medium and is supplemented with a carbon source and a growth hormone. Any auxin may be used in this medium, such as for example, IAA, NAA and IBA. In one embodiment, gibberellic acid and a combination of glucose and sucrose is used. Gibberellic acid may be used in the range of about 0.01–3.0 mg/l, preferably about 0.05–1.0 mg/l, and most preferably about 0.1–0.3 mg/l.

The pH of the novel culture media prepared and used according to the present invention is as generally known in the prior art. Preferably, the pH ranges from about 4.0 to about 6.0 and most preferably from about 5.5 to about 5.8. It is within the skill of a person of skill in the art to optimize the pH of the culture medium using the guidance of the present specification and general knowledge in the art.

The advantage of the methods of the present invention is that the total time required to produce somatic embryos and cacao plantlets is reduced in comparison with the methods known in the art. The amount of labor and the cost involved are greatly reduced. More significantly, the efficiency of somatic embryo production and plant regeneration from cacao explants is dramatically improved. In total, these improvements allow for the practical use of somatic embryogenesis for cacao clonal propagation and other applications that require the production of a large quantity of plants from limited source materials.

Agrobacterium-mediated Transformation

In the last decade, transformation technology has played an increasingly important role in the genetic manipulation of crop plants for their improvement and the study of the molecular mechanisms underlying plant gene expression and regulation. However, due to the lack of a useable transformation procedure, the application of such biotechnological approaches has not been possible for cacao. Successful transformation of cacao cells, and the subsequent production of transgenic somatic embryos and plants using the Agrobacterium-mediated transformation procedures as described herein, provide a new procedure for the introduction of foreign genes into cacao and an alternative approach for the incorporation of novel mechanisms of resistance to viruses, fungi and insect pests. A "foreign gene" is intended to mean any gene or polynucleotide not naturally found in cacao. In addition, this technology enables the development of transgenic cacao varieties with improved agronomic performance characteristics, and provides a new experimental system for study of gene expression and function, in cacao. The use of cacao varieties improved via the utilization of transformation technology also facilitates the implementation of sustainable agricultural practices in cacao cultivation, and eventually helps maintain a healthy tropical forest ecosystem.

Transgenic cacao plants may be produced according to the method of the invention having the following steps: (i) culturing Agrobacterium in low-pH induction medium at low temperature and preconditioning, i.e., coculturing bacteria with wounded tobacco leaf extract in order to induce a high level of expression of the Agrobacterium vir genes whose products are involved in the T-DNA transfer; (ii) coculturing cacao tissue explants, including zygotic and/or somatic embryo tissues derived from cultured explants, with the incited Agrobacterium; (iii) selecting transformed callus tissue on a medium containing antibiotics; and (v) and converting the embryos into plantlets.

Figure 11:
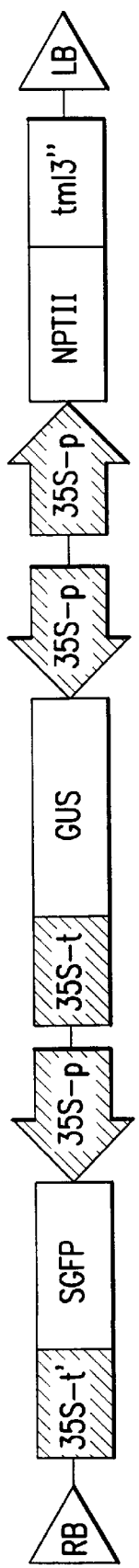
FIG. 11 depicts the T-DNA region of the binary vector pDM96.0501. RB and LB represent the right and left border of T-DNA, 35S-p and 25S-t represent the CaMV35S promoter and terminator, SGFP represents the green fluorescent protein gene, GUS represents the beta-glucuronidase gene, NPTII represents the neomycin phosphotransferase genes, and tml3' represents the tumor morphology large gene terminator.

Any non-tumorigenic *A. tumefaciens* strain harboring a disarmed Ti plasmid may be used in the method of the invention. Any Agrobacterium system may be used. For example, Ti plasmid/binary vector system or a cointegrative vector system with one Ti plasmid may be used. Also, any marker gene or polynucleotide conferring the ability to select transformed cells, callus, embryos or plants and any other foreign gene such as for example a gene conferring resistance to a disease may also be used. A person of skill in the art can determine which markers and foreign genes are used depending on particular needs. For example, *A. tumefaciens* strain EHA101 harboring a disarmed version of the atropine-type supervirulent Ti plasmid pTiBo542 (Hood et al. 1986. J Bacteriol 168:1291–1301) and a binary vector pDM96.0501 (shown in FIG. 11) may be used.

For purposes of the present invention, "transformed" or "transgenic" means that at least one marker gene or polynucleotide conferring selectable marker properties is introduced into the DNA of cacao cell, callus, embryo or plant. Additionally, any foreign gene may also be introduced.

To increase the infectivity of the bacteria, Agrobacterium is cultured in low-pH induction medium, i.e., any bacterium culture media with a pH value adjusted to from 4.5 to 6.0, most preferably about 5.2, and at low temperature such as for example about 19–30° C., preferably about 21–26° C. The conditions of low-pH and low temperature are among the well-defined critical factors for inducing virulence activity in Agrobacterium (E.g. Altmorbe et al. (1989) Mol. Plant-Microbe. Interac. 2:301–308; Fullner et al. (1996) Science 273:1107–1109; Fullner and Nester (1996) J. Bacteriol. 178:1498–1504).

The bacteria is then preconditioned by coculturing with wounded tobacco leaf extract to induce a high level of expression of the Agrobacterium vir genes. The preconditioning with tobacco extract is known in the art and is described in detail in Example 3. The vir genes are involved in the T-DNA transfer process as generally known in the art. The wounded tobacco leaf extract is prepared as generally known in the art.

Agrobacterium treated as described above is then cocultured with cacao tissue explants, such as for example zygotic and/or somatic embryo tissue. Somatic embryos may be obtained according to the present invention as described above. Cacao explants are then cultured on a liquid, semi-solid or solid tissue culture medium containing selective antibiotics to obtain transformed callus masses. The above-described PCG and SCG media may be used in this process according to the steps described under "Methods of Inducing Somatic Embryos." The transformed callus may be identified based on any selective marker such as for example expression of the kanamycin-resistance gene (NPTII) and the green fluorescent protein (GFP) gene, incorporated in the T-DNA region of the binary vector.

In the next step, transgenic somatic embryos are induced from the recovered transformed calli. The above-described embryo development medium and culture procedure may be used.

In the final steps, embryos are converted and cacao plantlets are regenerated using a combination of a primary and secondary embryo conversion media, a plant regeneration medium described above or any other medium useful for embryo conversion and regeneration of plantlets.

The culture media used in the invention contain an effective amount of each of the above described medium components (e.g. basal medium, growth regulator, carbon source). For purposes of the present invention, an "effective amount" of a given medium component is the amount necessary to cause a recited effect. For example, an effective amount of a growth hormone in the primary callus growth medium is the amount of the growth hormone that induces callus formation when combined with other medium components. Other compounds known in the art to be useful for tissue culture media, such as for example vitamins and gelling agents, may also be used as optional components of the culture media of the invention.

The present invention also relates to cacao somatic embryos and plants, as well as transformed somatic embryos and transformed plants obtained using the methods described herein.

The invention is further described by the following non-limiting examples.

EXAMPLE 1

Materials and Methods

Chemicals from Sigma Chemical Co., St. Louis, Mo. were used for all media preparation. Calcium hypochlorite [$Ca(OCl)_2$] was obtained from Aldrich Chemical Company, Inc. (Milwaukee, Wis.). The pH of the medium was adjusted using 1N KOH, prior to autoclaving. All media were autoclaved for 20 min at 121° C.

A powdered form of the DKW medium developed by Driver and Kuniyuki (Driver, J. A. and Kuniquki, A. H., (1984) Hortsci 19: 507–509) and Tulecke and McGranahan (Tulecke, W. and McGranaham, G., (1985) L. Plant Sci 40: 57–63) was obtained from Sigma Chemical Co. (D-6162). However, due to the hygroscopic nature of the powdered preparation, stock solutions containing the chemical components of the DKW medium were used for medium preparation. Macronutrients of the DKW medium were separated into stock solutions A and B to avoid chemical interactions between inorganic salts at high concentrations, and to prevent precipitation of salts during storage.

DKW 10× macro solution A was prepared by combining (per liter) 14.16 g $NH_4NO_3$ and 19.68g $Ca(NO_3)_2.4H_2O$. DKW 10× macro solution B was prepared by combining the following compounds (per liter): 1.49 g $CaCl_2.2H_2O$, 15.59 g $K_2SO_4$, 7.4 g $MgSO_4.7H_2O$, and 2.65 g $KH_2PO_4$. DKW 100× micro solution was prepared by combining the following compounds (per liter): 1.7 g $Zn(NO_3)_2.6H_2O$, 3.34 g $MnSO_4.H_2O$, 3.38 g $FeSO_4.7H_2O$, 9.54 g Na-EDTA, 0.48 g $H_3BO_3$, 25 mg $CuSO_4.5H_2O$, and 39 mg $Na_2MoO_4.2H_2O$. DKW 1000× vitamin solution was prepared by combining the following compounds (per liter): 10 g myo-inositol, 0.2 g thiamin-HCl, 0.1 g nicotinic acid, and 0.02 g glycine.

Fresh stock solutions of growth regulators (e.g. TDZ and 2,4-D), were prepared every 3 months. TDZ solution was prepared by dissolving 5 mg thidiazuron in 1 ml of 1N KOH and $dH_2O$. 24-D solution was prepared by dissolving 10 mg 2,4-dichlorophenoxyacetic acid in 1 ml 100% ethanol and adding $dH_2O$. Kinetin solution was prepared by dissolving 10 mg kinetin in 1 ml of 1N NaOH and adding $dH_2O$. 6-BA solution was prepared by dissolving 10 mg 6-benzylaminopurine in 1 ml of 1N NaOH and adding deionized water.

Primary callus growth (PCG) medium was prepared by combining the following solutions and compounds (per liter): 100 ml each DKW macro solutions A and B, 10 ml DKW micro solution, 1 ml DKW vitamin solution, 20 g glucose, 250 mg glutamine, 100 mg myo-inositol, 100 ml 2,4-D solution, 10 ml TDZ solution, and 2.0 g phytagel, and the pH was adjusted to 5.8.

Secondary callus growth (SCG) medium was prepared by combining the following solutions and compounds: 2.3 g McCown's woody plant basal salt mixture (Lloyd, D. and McCown, B., (1981) Proc Int Plant Prop Soc 30: 421427) (available from Sigma M-6774), 1.0 ml Gamborg's vitamin solution (Gamborg, O. L., (1966) Can J Biochem 44: 791–799) (available from Sigma G-1019), 20.0 g glucose, 200 µl 2,4-D solution (=2.0 mg/l), 30 µl kinetin solution (=0.3 mg/l), 50 ml coconut water, and 2.2 g phytagel, and the pH was adjusted to 5.8.

Embryo development (ED) medium was prepared by combining the following solutions and compounds (per liter): 100 ml each DKW macro solutions A and B, 10 ml DKW micro solution, 1 ml DKW vitamin solution, 20 g sucrose, 1.0 g glucose, and 2.0 g phytagel, and the pH was adjusted to 5.8. Autoclaved ED medium often solidified quickly at a relatively high temperature (lower than 40° C.), possibly due to its high content of calcium salts that may trigger chemical reactions with phytagel. Thus, precaution must be taken during distribution of the autoclaved medium into culture plates, in order to prevent over-cooling and premature solidification of the medium.

MSG medium was prepared by combining the following solutions and compounds (per liter): 4.44 g MS basal salts (Murashige, T. and Skoog, F., (1962) *Physiol Plant* 15:473–497) with Gamborg's vitamins (Gamborg, O. L., (1966) *Can J Bioichem* 44:791–799), 20 g glucose, and 2 g phytagel, and the pH was adjusted to 5.8.

Plant regeneration (PR) medium was prepared by combining the following solutions and compounds (per liter): 20 ml each DKW macro solutions A and B, 2.0 ml DKW micro solution, 0.2 ml DKW vitamin solution, 10 g glucose, 5 g sucrose, 0.2 g $KNO_3$, and 1.7 g phytagel, and the pH was adjusted to 5.8.

Plant materials used were unopened immature cacao flower buds 5 to 8 mm in length (depending upon genotype), collected between 8 am and 11 am. Flower buds at advanced developmental stages, harvested in the afternoon may also be used. However, these buds open readily during surface-sterilization and may cause the contamination of explants. Flower buds collected during the morning remain closed throughout the surface-sterilization process, and are the preferred explants.

Experimental Procedure

Staminode and petal base tissues were used as culture explants (FIG. 2). Although immature flower buds with a range of sizes can be collected, large flower buds were chosen because such flower buds were easier to dissect and handle in the absence of a dissecting microscope. In addition, staminodes and petal base explants were separated from associated floral parts such as stamen filaments and petal tissue, in order to minimize possible interactions that may affect the in vitro growth of explants. It was found that stamen-derived calli were difficult to induce to produce somatic embryos, and that petal tissues turn brown quickly and released phytotoxic phenolic compounds into the medium.

a. Collection and surfacesterilzation of flower buds

Immature flower buds were collected in a 50-ml centrifuge tube containing cold water. A 1% (w/v) calcium hypochlorite solution was prepared by dissolving 0.5 g $Ca(OCl)_2$ in 50 ml sterile water in a sterile 50-ml centrifuge tube. The cold water was decanted from the centrifuge tube containing the immature flower buds inside the transfer hood and all of the flower buds were transferred into the sterile centrifuge tube containing the calcium hypochlorite solution. The flower buds were immersed in the calcium hypochlorite solution for 20 min. The hypochlorite solution was then removed and 40 ml sterile water was added to rinse the flower buds. The buds were rinsed at least three times and were then transferred to a Petri dish and the plate was covered to prevent desiccation.

b. Dissection of flower bud and callus induction

Two to three layers of sterile paper towels were placed in the transfer hood. Four flower buds on the top surface of the paper towels were blotted dry and then transferred onto a Petri dish cover. The flower buds were sliced across at a position of about ⅓ of the flower length from the base using a sterile scalpel blade. The staminodes and petal base tissues were extracted together from the top part of the flower bud using a pair of sterile forceps. Any attached petal tissue was removed from the petal base explants.

Figure 2A:
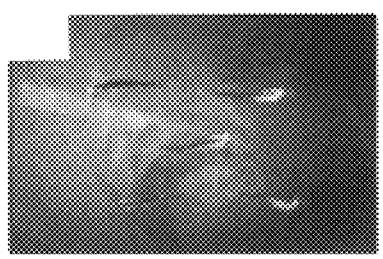
FIG. 2(a) is a photograph of cultured staminode explants.

The staminodes and petal base explants from the four flower buds were then transferred into a Petri dish containing 30 ml of PCG medium. Any fused staminodes and petal base explants were separated and explants were distributed evenly across the medium. The Petri dishes were sealed with a double layer of parafilm and cultures were maintained in the dark at 25±2° C. for 14 days (FIG. 2*a*). Growth reduction, senescence, and tissue browning may occur with subculture intervals longer than 14 days.

Figure 2B:
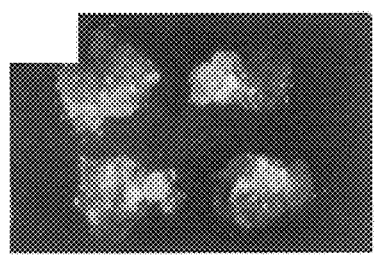
FIG. 2(b) is a photograph of embryonic callus induced from the entire staminode explant.

The staminode and petal base explants were then transferred from a PCG medium to a Petri dish containing 30 ml of SCG medium. The dishes were sealed and the cultures were maintained in the dark for 14 days at 25±2° C. Globular calli were produced on the entire tissue explant at the end of this culture period (FIG. 2*b*).

c. Somatic embryo induction and maintenance

Figure 2C:
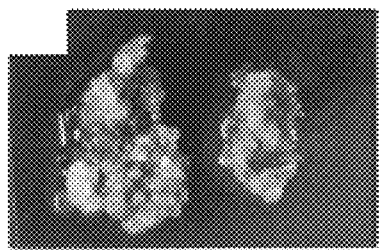
FIGS. 2(c), (d) and (e) are photographs of somatic embryos at various stages of development (globular, heart and torpedo-shaped embryos).
Figure 2D:
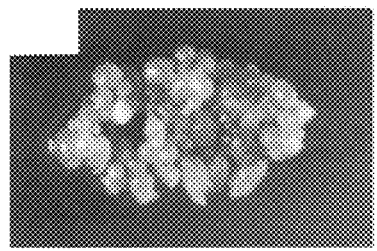
FIG. 2 shows certain steps in the process of culturing staminode explants inducing mature embryos and regenerating plantlets.
FIGS. 2(f) and (g) are photographs of mature embryos and converted plantlets respectively.
FIG. 2(h) is a photograph of somatic embryo-derived cacao plants grown in the greenhouse.

Staminode and petal base explants and calli derived in the callus induction step were transferred to Petri dishes containing 30 ml of ED medium. Explants were cultured in the dark for 14 days at 25±2° C. Explants were then subcultured onto the fresh ED medium and maintained in the dark for another 14 days. By that time, numerous somatic embryos at globular and heart-shaped stages of development were visible on the embryogenic calli (FIGS. 2*c* and *d*).

Figure 2E:
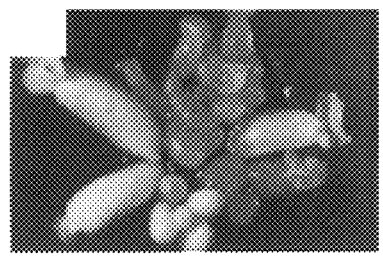
Figure 2F:
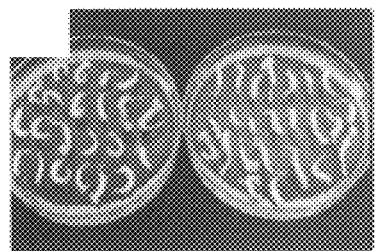

Somatic embryos were then excised from the callus tissue and transferred onto Petri dishes containing 30 ml of ED medium. Embryo cultures were maintained in the dark with a subculture interval of 14 days at 25±2° C., until somatic embryos reached maturity (FIG. 2*e*).

d. Embryo conversion and plant establishment.

Germinating somatic embryos with an extended radicle, preferably Type II embryos (FIG. 2*f*) were selected. The embryos were inserted vertically into PR medium in a Magenta vessel (80 ml/vessel). Four to five embryos were placed in each vessel. The vessel was sealed with low-temperature electric tape. Cultures were maintained under light (16-h photoperiod) at 25±2° C. for 14 days. Germinating embryos were subcultured to fresh PR medium every 14 days.

Figure 2G:
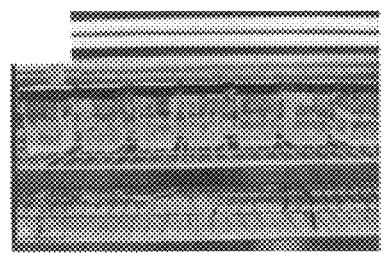

For Type I embryos, mature embryos about 1 cm in length, were selected and 30 transferred onto Petri dishes containing 30 ml MSG medium. Cultures were maintained under light with a 24-h photoperiod for 14 days. The embryos with roots and shoots that turned green were transferred onto PR medium in Magenta vessels (FIG. 2*g*). Cultures were maintained under light (16-h photoperiod) at 25±2° C. for 14 days. Germinating embryos were subcultured to fresh PR medium every 14 days.

Figure 2H:
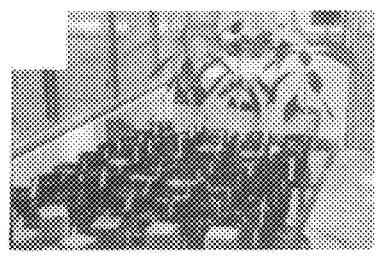

Plantlets with developing green leaves and healthy taproots were transferred into 4-inch plastic pots containing sterile Metro-Mix 300 soil mixture (FIG. 2*h*). Water was poured into the pot to saturate the soil mixture. The plantlet was covered using a magenta vessel. Plants were maintained in the greenhouse with an 80% humidity controlled by an automatic misting system. Water was added regularly to maintain an adequate moisture content for optimal plant growth. When the plantlet produced a new leaf, the cover vessel was removed. Regular amounts of fertilizers were applied to enhance plant growth (FIG. 2*h*).

Experimental Results

A key to the successful development of a highly efficient somatic embryogenesis system for cacao was the discovery and use of a series of improved culture conditions throughout the entire procedure. In all previous studies of somatic embryogenesis in cacao, the MS medium (Murashige and Skoog, (1962) *Physiol Plant* 15:473–497) that was previously developed for the in vitro culture of tobacco tissue, was employed as the main source of inorganic nutrients for cacao cell growth. However, the use of this medium was in fact one of the major limitations in cacao tissue culture. The DKW medium, which was formulated for somatic embryogenesis and plant regeneration in woody perennials, provided a better balanced composition of nutrients for cacao. In this experiment, the use of DKW medium was essential for obtaining embryogenic cultures and for maintaining normal growth and development of cacao somatic embryos.

Figure 1B:
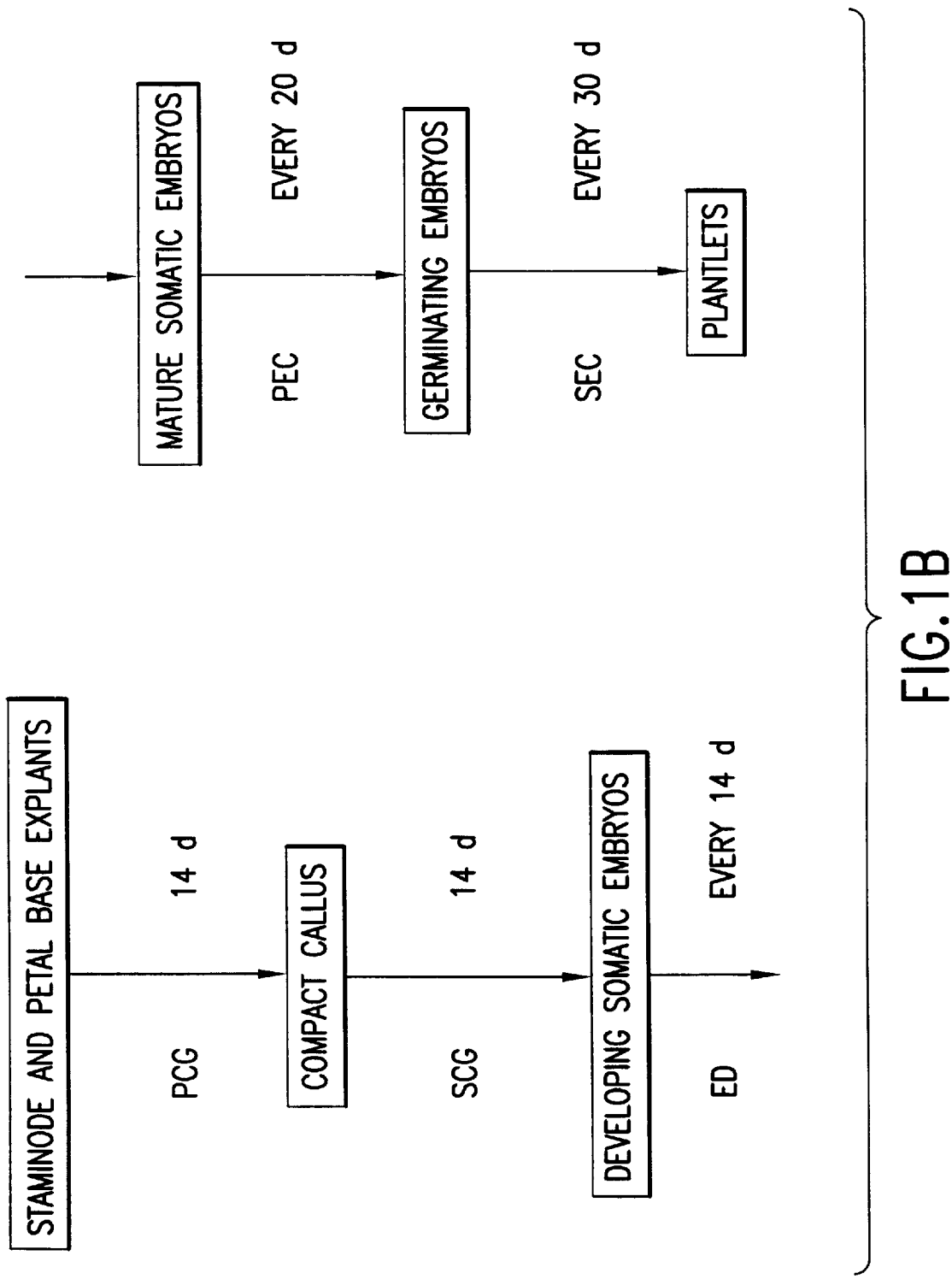
FIG. 1B represents a schematic outline of cacao plant regeneration in tissue culture according to one embodiment of the invention.

High frequencies of somatic embryo production and plant regeneration from cultured floral explants were readily obtained. A schematic outline of cacao somatic embryogenesis used in this experiment is shown in FIG. 1. Photographs which show efficient somatic embryogenesis and plant regeneration from cultured staminode tissues of cacao through depiction of the various products obtained throughout the stages of the procedure are shown in FIG. 2.

Figure 3:
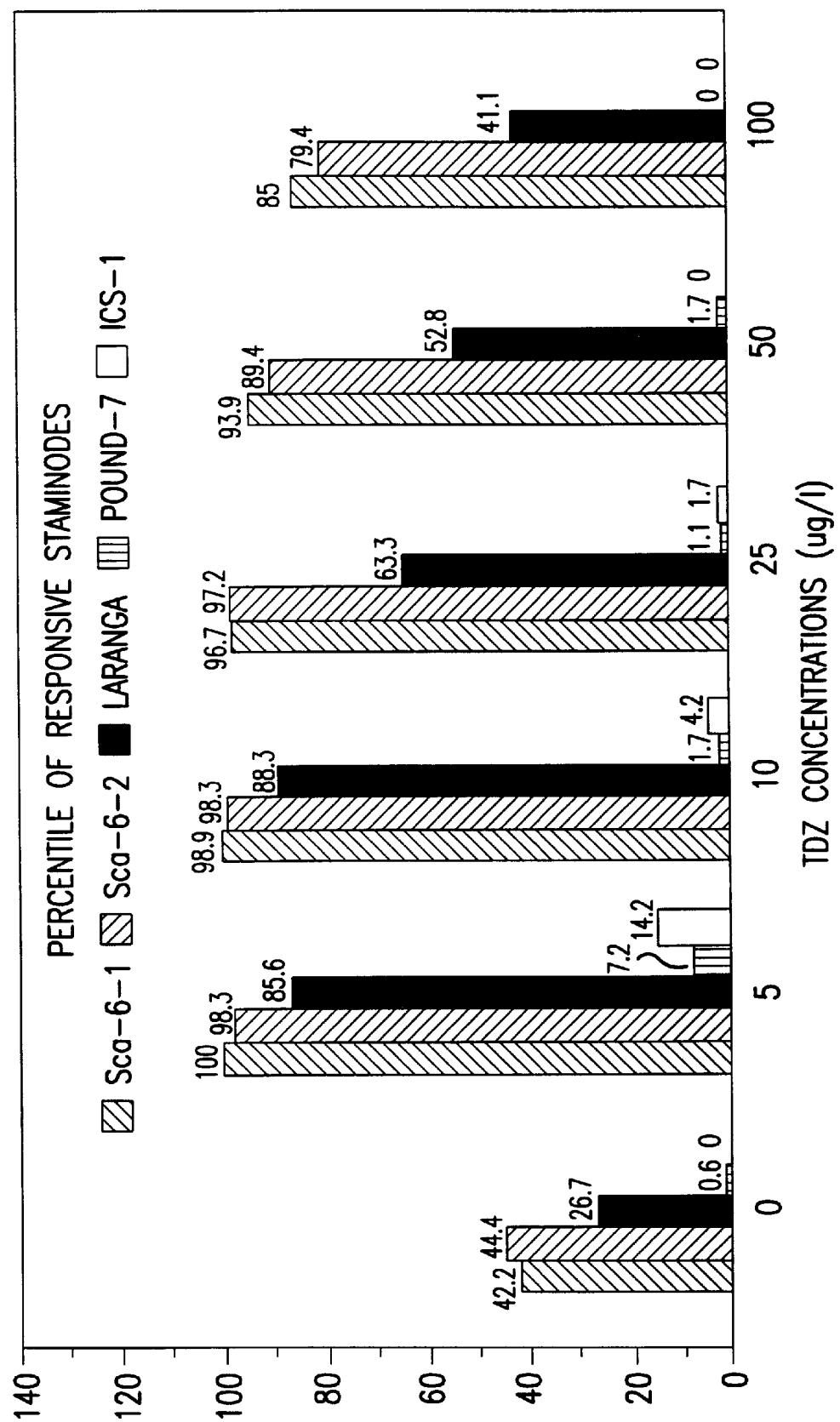
FIG. 3 is a graph representing the effects of TDZ concentration on somatic embryogenesis from staminode explants for five cacao genotypes using the culture procedures according to one embodiment of the invention. The percentile of responsive staminodes at each TDZ concentration is shown above the bars.

The effect of TDZ concentration on somatic embryogenesis from staminode explants of five cacao genotypes was determined and is shown in FIG. 3. Staminodes were cultured on PCG medium containing various concentrations of TDZ. Embryonic calli were subcultured onto SCG medium and somatic embryos were subsequently induced by culturing calli on ED medium. Data were collected two months after culture initiation. Each treatment contained 20 staminodes per plate with three replicate plates. The values shown in FIG. 3 represent the average percentage rates of embryo-producing staminodes from three repeated experiments. Up to 100% of cultured staminode and over 60% of petal base explants from cacao genotype Sca-6 produced somatic embryos (FIG. 3).

Figure 4:
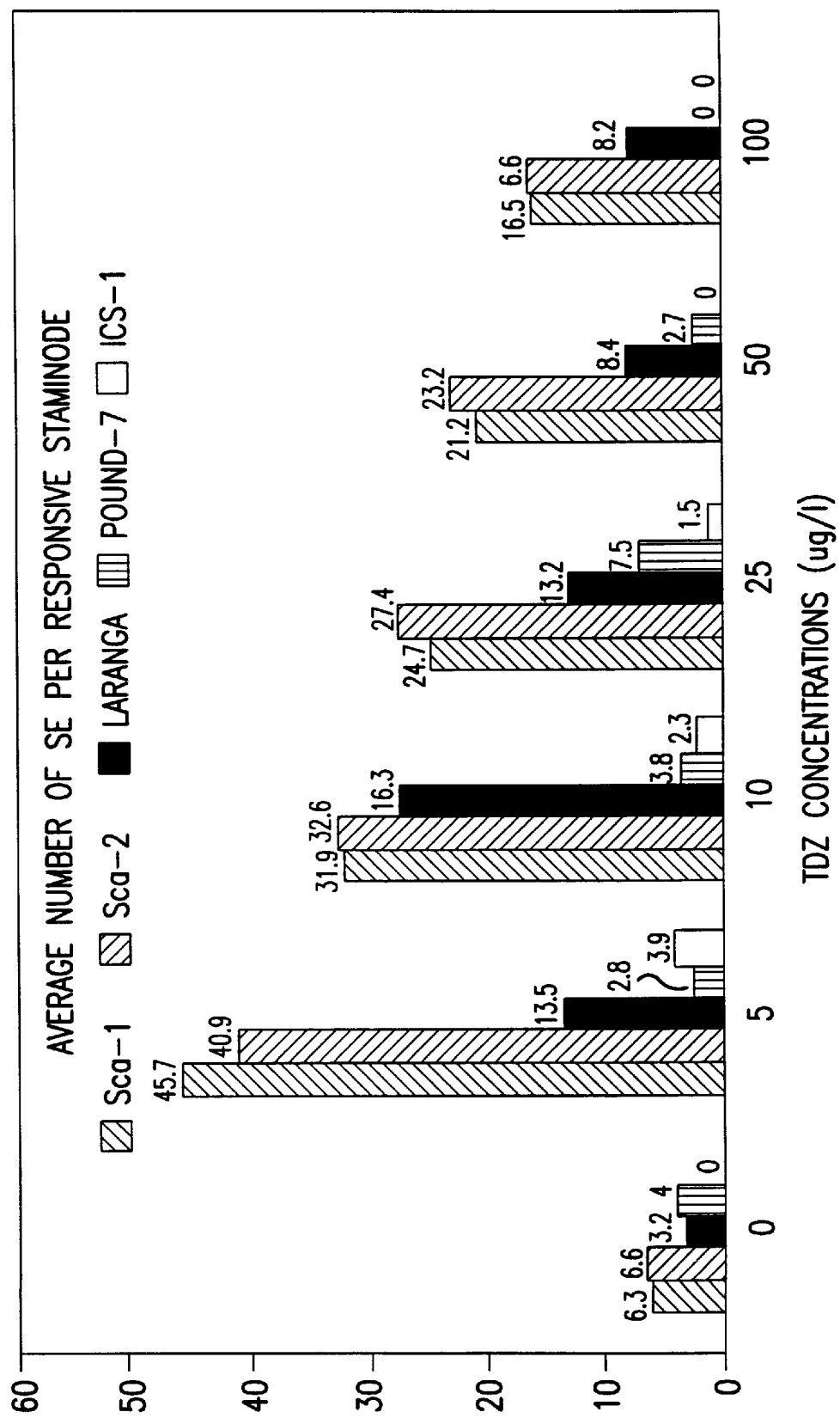
FIG. 4 is a graph representing the effects of TDZ concentration on somatic embryo production from staminode explants for five cacao genotypes using the culture procedures according to one embodiment of the invention. The average number of somatic embryos per responsive staminode at each TDZ concentration is shown above the bars.

The effect of TDZ concentration on somatic embryo production from staminode explants of five cacao genotypes was determined and is shown in FIG. 4. Staminodes were cultured on PCG medium containing various concentrations of TDZ. Embryogenic calli were subcultured onto SCG medium and somatic embryos were subsequently induced by culturing calli on ED medium. Data were collected two months after culture initiation. Each treatment contained 20 staminodes per plate with three replica plates. Values represent the average number of somatic embryos per responsive staminode from three repeated experiments. A single Sca-6 staminode explant produced up to 140 and an average of about 46 primary somatic embryos (FIG. 4).

Figure 5:
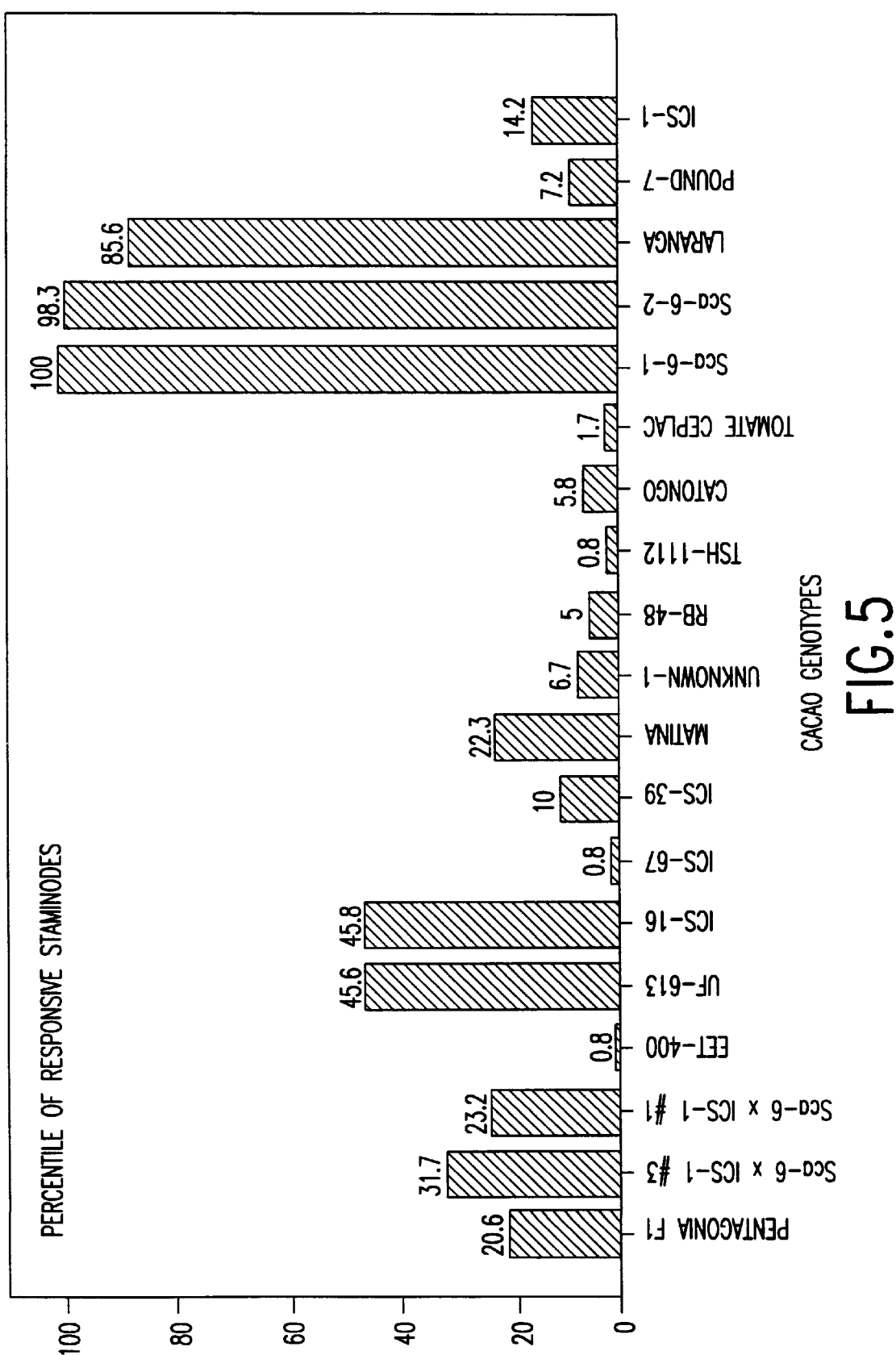
FIG. 5 is a graph representing the percentile of staminodes responsive to somatic embryo formation from staminode explants of 19 tested cacao genotypes using the culture procedures according to one embodiment of the invention.

The level of somatic embryo formation from staminode explants of 19 tested cacao genotypes was determined and is shown in FIG. 5. Embryogenic calli were induced and propagated on PCG and SCG media, respectively. Somatic embryos were induced by culturing calli on ED medium. Data were collected two months after initiation. Each treatment contained 20 staminodes per plate with three replicate plates. Values represent the average percentage rates of embryo-producing staminodes from two to three repeated experiments.

Figure 6:
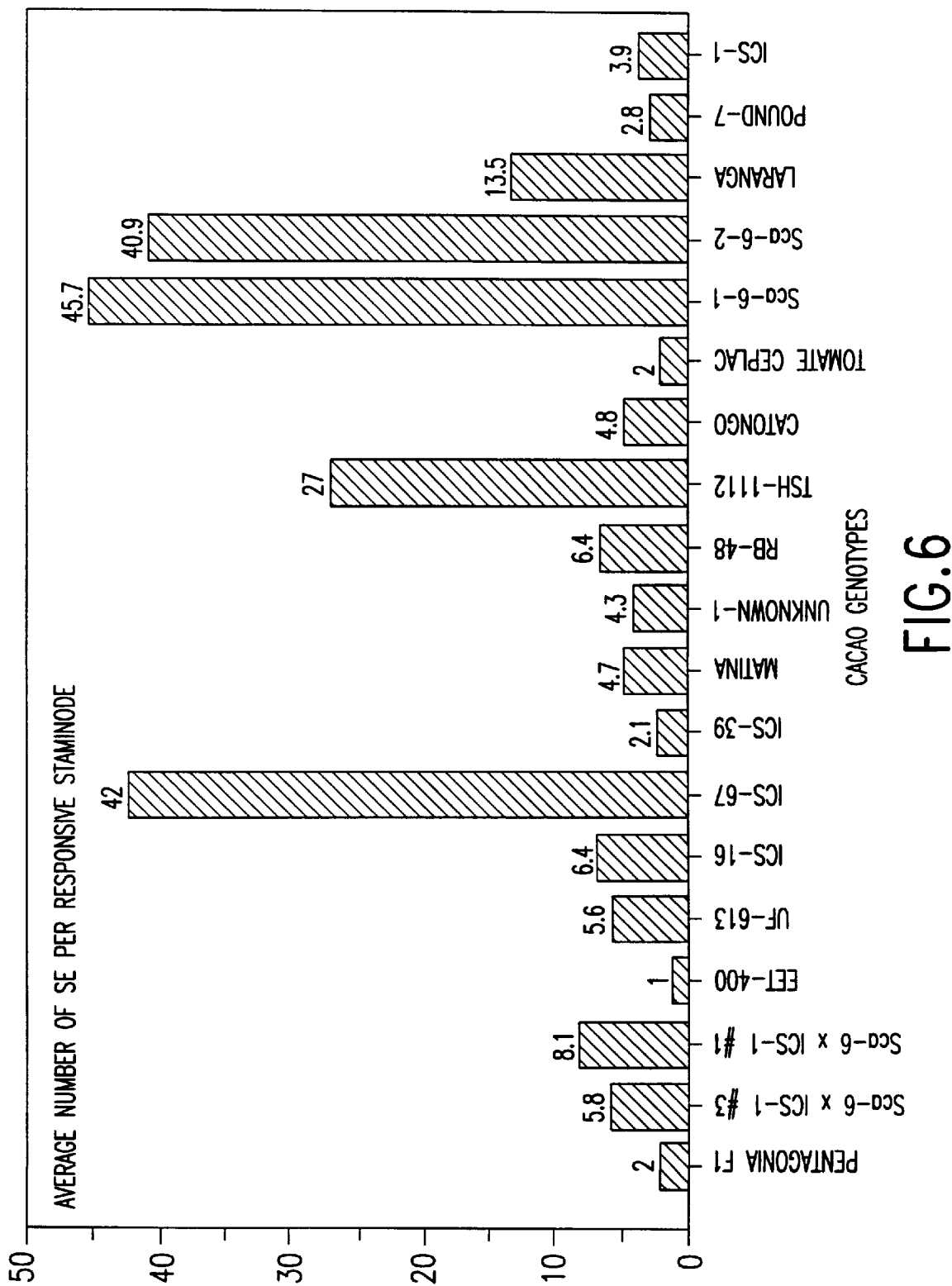
FIG. 6 is a graph representing the average number of somatic embryos produced from responsive staminode explants of 19 tested cacao genotypes using the culture procedures according to the invention.

The average number of somatic embryos produced from responsive staminode explants of 19 tested cacao genotypes was determined and is shown in FIG. 6. Embryogenic calli were induced from staminode explants on PCG medium for 14 days and propagated on SCG medium for another 14 days. Somatic embryos were subsequently induced by culturing staminode-derived calli on ED medium. The number of somatic embryos from each responsive staminode explant was determined two months after culture initiation. Each treatment contained 20 staminodes per plate with three replicate plates. Values represent the average number of somatic embryos per responsive staminode from two to three repeated experiments.

The results of FIGS. 5 and 6 indicate that the success of the procedure was genotype-independent. All 19 tested cacao genotypes produced somatic embryos.

Important factors in the invention included the use of TDZ and glucose as sources of cytokinin and carbon, respectively for the initiation of highly embryogenic cultures of cacao. TDZ possesses a strong cytokinin-like activity exceeding most of other commonly used cytokinins including zeatin, BA, and kinetin, and is highly resistant to degradation by cytokinin oxidase. However, over the years TDZ had not been tested for somatic embryogenesis in cacao. The invention devised for the first time the proper means to utilize this potent and stable compound for effective induction of embryogenic callus from cacao floral explants and subsequent efficient production of somatic embryos (FIGS. 3 and 5). In all previous studies of cacao somatic embryogenesis, sucrose and maltose were used as the main carbon source. The use of glucose as a major carbon source in the invention resulted from the observation that cacao tissues cultured on glucose-containing medium grew normally and did not produce any hypersensitive reactions that often lead to tissue senescence and cell death as frequently observed in cultures using other sugars.

Two types of somatic embryos were identified based on the following characteristics: Type I embryos had a yellowish and vitrified appearance, and an expanded embryo axis. During extended culture on ED medium, mature Type I embryos tended to 25 remain dormant. After transfer to embryo conversion medium, these embryos showed extensive cotyledonary growth, followed by the development of true leaves. Root development in germinating Type I embryos was normally slow. Type II somatic embryos were whitish in color and had a defined embryonic axis structure. These embryos underwent spontaneous germination upon reaching maturity on ED medium. After transfer to embryo conversion medium, these embryos turned green quickly, exhibited a significant hypocotyl elongation, and produced a strong taproot, within a short period of time. Epicotyl elongation and production of true leaves often occurred 2 to 3 weeks after transfer. The plant regeneration responses of these two types of cacao somatic embryos using previously defined culture conditions are summarized in Table 3 which shows data in which mature somatic embryos of cacao genotype Sca-6 were cultured on PR medium in Magenta vessels. Data were collected two months after culture initiation. Up to 73% of the selected mature somatic embryos that were produced using this procedure were capable of conversion into plantlets (Table 3).

TABLE 3

| Plant Regeneration Response of Two Types of Somatic Embryos of Cacao | | | | |
|---|---|---|---|---|
| Embryo Type | Type I | % | Type II | % |
| Total No. of SE | 96 | — | 191 | — |
| SE with root | 31 | 32.3 | 183 | 95.8 |
| SE with shoot | 26 | 27.1 | 140 | 73.3 |

EXAMPLE 2

Materials and Methods

Materials and methods were as described in Example 1 with the following exceptions.

In the secondary callus growth medium, kinetin and coconut water were replaced by 5 µl of 6-BA stock solution (=0.05 mg/l).

Primary embryo conversion (PEC) medium was prepared by combining the following solutions and compounds (per liter): 100 ml DKW macro solutions A and B, 10 ml DKW micro solution, 1 ml DKW vitamin solution, 0.3 g $KNO_3$, 1 ml amino acid solution, 20 g glucose, and 1.75 g phytagel, and the pH was adjusted to 5.8. Amino acid 100× solution for use in the primary embryo conversion medium was prepared by combining the following compounds (per 100 ml): 43.55 mg arginine, 18.76 mg glycine, 32.8 mg leucine, 45.65 mg lysine, and 51.05 mg tryptophane.

Secondary embryo conversion (SEC) medium was prepared by combining the following solutions and compounds (per liter): 25 ml each DKW macro solutions A and B, 2.5 ml DKW micro solution, 0.25 ml DKW vitamin solution, 5.0 g glucose, 2.5 g sucrose, 0.2 g $KNO_3$, and 1.75 g phytagel, and the pH was adjusted to 5.8.

Experimental Procedure

Steps a, b, and c were performed as described in Example 1. Step d was as described below.

d. Embryo conversion and plant establishment

Mature somatic embryos (generally up to 2 cm in length) with distinctive cotyledons or with an extended radicle (about 0.5 cm in length), including both Type I and Type II embryos (FIG. 2f) were selected. Ten to fifteen embryos were placed horizontally on PEC medium, in the Petri dishes. The culture dishes were sealed with a double layer of parafilm and maintained under light (16-h photoperiod) at 25±2° C. for 20 days. Germinating embryos were subcultured to fresh PEC medium every 20 days until the emergence of shoot growth was observed.

Shoot-producing embryos with two green leaves of at least 1 cm in length were transferred to SEC medium in Magenta vessels. The embryos were placed horizontally on the surface of the medium at a density of 4 to 6 embryos per vessel. Culture vessels were sealed with a double layer of parafilm. Cultures were maintained under light with a 16-h photoperiod for 30 days. Embryos that produced no roots or weak roots shorter than about 2 cm were transferred onto fresh SEC medium. Plantlets with roots longer than 2 cm were left in the culture vessel to avoid breakage of the delicate root system due to transfer handling. These plantlets can be maintained in the same culture vessel for up to 4 months without any adverse effects on plant growth and development (FIG. 2g).

Plantlets with developing green leaves of more than 3 cm in length and healthy roots of more than 2 cm in length were transplanted into 4-inch plastic pots containing autoclaved pre-moistened Metro-Mix 500 soil mixture (FIG. 2h). Water was poured into the pot to saturate the soil mixture. Plantlets were maintained in the greenhouse with 90% humidity controlled by an automatic misting system. Water was added regularly to maintain an adequate moisture content for optimal plant growth. When the plantlet produced a new leaf, regular amounts of fertilizers were applied to enhance plant growth (FIG. 2h).

Experimental Results

Figure 7:
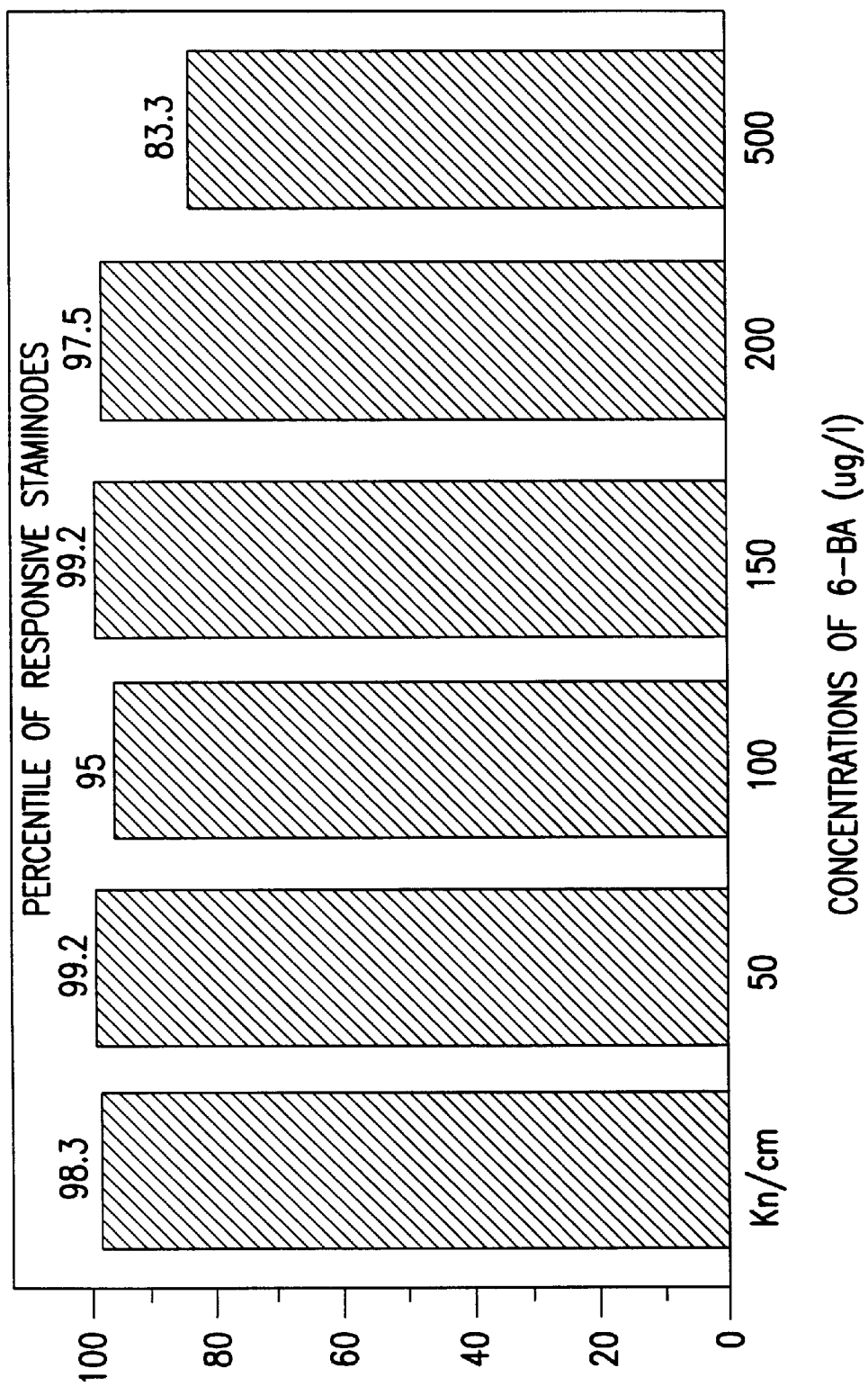
FIG. 7 is a graph showing the effect of the concentration of 6-benzylaminopurine in the secondary callus growth medium on the frequency of somatic embryo production from staminodes.

The influence of the concentration of 6-benzylaminopurine (6-BA) used in the SCG medium on the frequency of somatic embryo production from cacao staminodes was determined and is shown in FIG. 7. Rapidly growing calli were initiated from staminode explants on PCG medium and then transferred onto SCG medium containing various concentrations of 6-BA. A control treatment using SCG medium containing kinetin and coconut water (Kn/cm) was included. Somatic embryos were induced by culturing embryonic calli on ED medium. Data were collected two months after culture initiation. Each treatment contained 20 staminodes per culture plate with three replicate plates per experiment. Bar values represent the average percentage rates of embryo-producing staminodes from two independent experiments.

Figure 8:
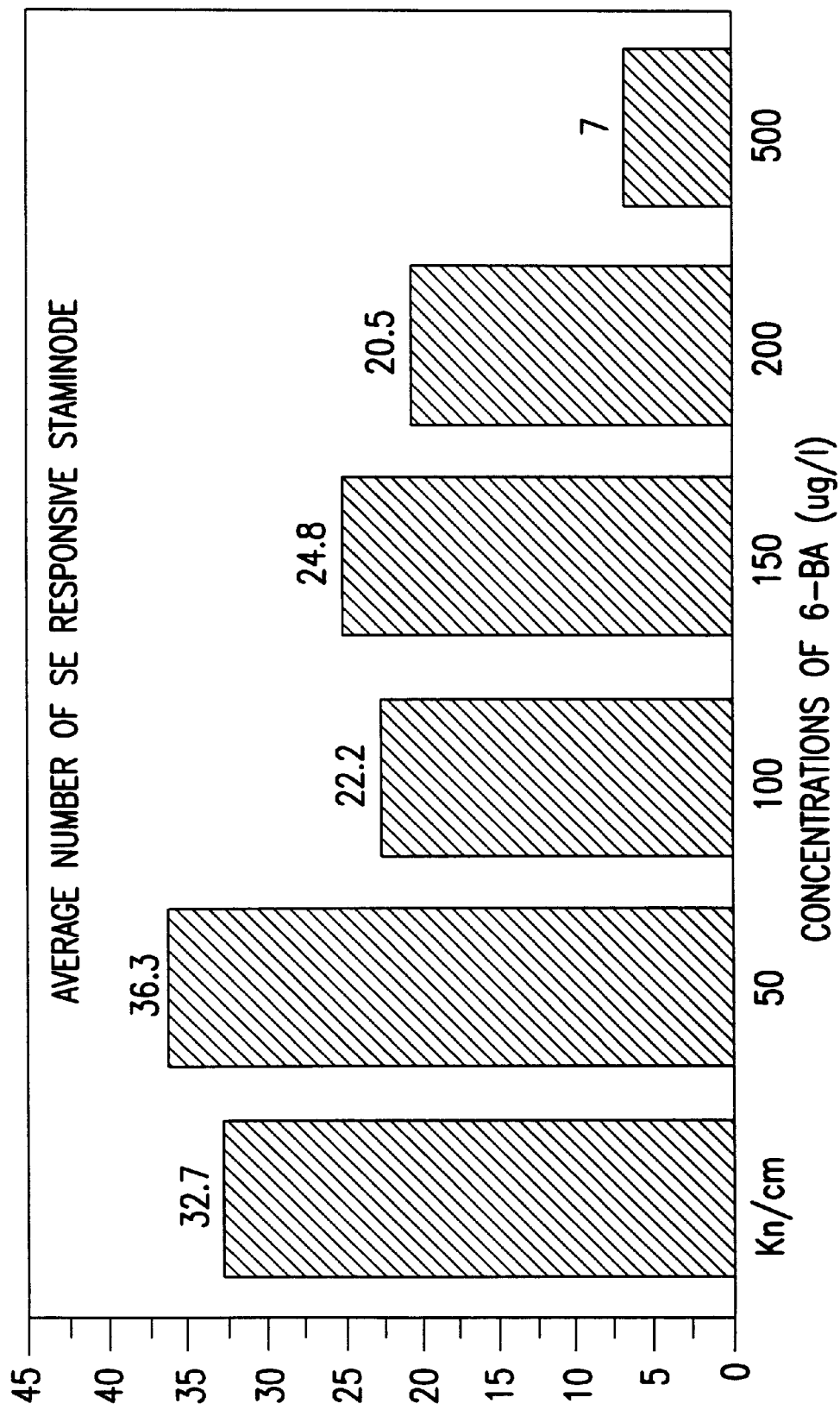
FIG. 8 is a graph showing the effect of the concentration of 6-benzylaminopurine in the secondary callus growth medium on the average number of somatic embryos produced per responsive staminode explant.

The influence of the concentration of 6-BA used in the SCG medium on the production of somatic embryos from cacao staminode explants of Sca-6 was determined and is shown in FIG. 8. Rapidly growing calli were initiated on PCG medium and then transferred onto SCG medium containing various concentrations of 6-BA. A control treatment using SCG medium containing kinetin and coconut water (Kn/cm) was included. Somatic embryos were induced by culturing embryogenic calli on ED medium. Data were collected two months after culture initiation. Each treatment contained 20 staminodes per culture plate with three replicate plates per experiment. Bar values represent the average number of somatic embryos produced from each embryo-producing staminode from two independent experiments.

In addition, efficient repetitive embryogenesis was also obtained. A single primary embryo produced more than 50 secondary embryos after being subjected to an extended culture period of one month (data not shown).

EXAMPLE 3

The following example describes an applications of the above-described Agrobacterium-mediated transformation of cacao using A. tumefaciens strain EHA101 harboring a disarmed version of the atropine-type supervirulent Ti plasmid pTiBo542 (Hood et al. 1986. *J Bacteriol* 168:1291–1301) and a binary vector pDM96.0501 and staminode-derived somatic embryos as inoculation explants.

Materials and Methods

A binary plasmid, pDM96.050, 1, which contains three transgenes (SGFP-TYG, GUS and NPTI1 genes, all under control of CaMV35S promoter) within the T-DNA region and a gentamycin-resistance gene in the plasmid backbone (FIG. 3) was obtained from Calgene Inc., Davis, Calif. The plasmid was introduced into A. tumefaciens strain EHA101 for use in cacao transformation.

Chemicals from Sigma Chemical Co., St. Louis, Mo., Fisher Scientific, Pittsburgh, Pa., and Difco Laboratories, Detroit, Mich. were used for all media preparation. The pH of the media was adjusted using IN KOH solution, prior to autoclaving. All media were autoclaved for 20 min at 121° C.

The preparation of DKW stock solutions and embryo development (ED) medium was as described in Example 1.

YEP5 medium was prepared by combining 10.0 g peptone, 10.0 g yeast extract, and 5.0 g NaCl. The pH was adjusted to 5.2.

Agrobacterium inoculation (AI) medium was prepared (per liter) by combining 0.88 g MS basal salts plus Gamborg's vitamins (Sigma medium preparation, Cat. No. M-0404) and 10 g glucose. The pH was adjusted to 5.3.

Primary selection (PS) medium was prepared (per liter) by combining ED medium with 400 mg Claforan (i.e., cefotaxime sodium available from Hoechst-Russel Pharmaceutical Inc., Somerville, N.J.).

Secondary selection (SS) medium was prepared (per liter) by combining ED medium without phytagel, 400 mg Claforan, and 200 mg kanamycin.

Tobacco propagation (TP) medium was prepared (per liter) by combining 4.4 g MS basal salts plus Gamborg's vitamins, 30.0 g sucrose, and 2.2 g phytagel. The pH was adjusted to 5.8.

Plant materials used were: In vitro grown tobacco (*Nicotiana tabacum* cv. Xanthi) and Cacao somatic embryos at heart- and torpedo-shaped stages of development.

Experimental Procedure a. Preparation of bacterial culture and inoculation of cacao somatic embryos Prior to inoculation of cacao somatic embryos, Agrobacterium cells were treated with tobacco extract prepared from wounded leaf tissues of in vitro grown tobacco plants. To achieve optimal stimulation of the expression of Agrobacterium vir genes by wound-induced metabolites and other cellular factors, tobacco leaves were wounded and pre-cultured overnight. Culturing of bacteria in low pH medium and at low temperature was used to further enhance the bacteria vir gene expression and infectivity.

Cacao somatic embryos were produced following the procedures described in Examples 1 and 2. Healthy whole embryos of about 4 to 8 mm in size, at heart- and torpedo-shaped developmental stages were used for transformation. In order to reduce the phytotoxic effects to embryo growth, any embryos with brown spots containing phenolics compounds or dying tissues were eliminated from the transformation materials.

Twenty-four hours before the transformation experiment three to five leaves were removed from in vitro grown tobacco plants and collected in a Petri dish. In vitro tobacco plants were maintained in Magenta vessels containing 80 ml of TP medium at 25° C. with a lighting regime of 16 hours and a light intensity of about 40 mmol×m-2 x s-1. Tobacco plants were subcultured every 20 days by cutting and transferring shoot tips with 2 to 3 expanded leaves to fresh medium. The tobacco leaves were cut into small pieces (0.5 $cm^2$). Leaf pieces were spread evenly across the surface of a Petri dish containing 25 ml of TP medium. A total of 5 g of leaf tissue was prepared in this manner. The Petri dishes were sealed and cultured overnight in the dark.

One ml of *A. tumefaciens* stock solution was inoculated into 30 ml of YEP5 medium supplemented with 50 mg/l kanamycin and 20 mg/l gentamycin. Bacteria were cultured overnight at 25° C. in the dark on a gyratory shaker at 100 rpm. When the bacteria density reached an $OD_{600}$ of 1.0 to 1.5, the cells were harvested by centrifugation at 7000 rpm at 20° C. for 10 min. The supernatant was discarded and the bacteria were resuspended in 20 ml AI medium in a sterile flask. Five grams of pre-cultured tobacco leaf tissue was transferred to a sterile mortar. Two ml of sterile water was added. Leaf tissue was ground into a fine slurry. The aqueous solution (about 5 ml) was transferred from the slurry to the flask containing the Agrobacterium using a sterile transfer pipet. The bacteria mixture was cultured at 22° C. in the dark on a shaker at 100 rpm for 3 hours.

About 100 healthy intact embryos were selected from somatic embryo cultures prepared according to the procedures of Examples 1 and 2. Unlike the common practices used in Agrobacterium-mediated transformation of other plant species, it is not necessary to wound the cacao somatic embryos before Agrobacterium infection. Wounding embryo tissue induces the production of phenolic compounds and results in reduced infection rate.

The developmental stages of cacao somatic embryos can influence the transformation efficacy. According to the applicants' transient gene expression experiments, the use of heart-shaped embryos resulted in the highest transformation frequency, followed by torpedo-shaped embryos, while the globular embryos tended to die easily, probably due to the smaller tissue size and lower tolerance to physical wounding and stress caused by the Agrobacterium infection (FIG. 4). Thus, the use of heart- and torpedo-shaped embryos for transformation is preferred. Embryos were transferred to a Petri dish. About 30 ml of pretreated Agrobacterium culture was poured into the Petri dish. Forceps were used to ensure immersion of all explants into the suspension. The Petri dish was covered and placed in a vacuum desiccator. Vacuum pressure was applied for 1 min. The vacuum was slowly released. The liquid solution was removed completely using a sterile transfer pipet. The embryos were placed on the surface of a piece of sterile paper towel for a few seconds to remove the remaining solution. The embryos were transferred to Petri dishes containing 30 ml of ED medium (30 embryos per plate). The Petri dishes were covered and sealed. The Petri dishes were incubated at 25° C. in the dark for 24 hours.

b. Detection of GFP expression and selection for transformants

GFP was used to monitor the transient expression of transgenes in cacao cells soon after Agrobacterium-mediated transformation and to facilitate the identification of explants containing transformed cells for subsequent selection for stable transformants using liquid culture medium.

Figure 13:
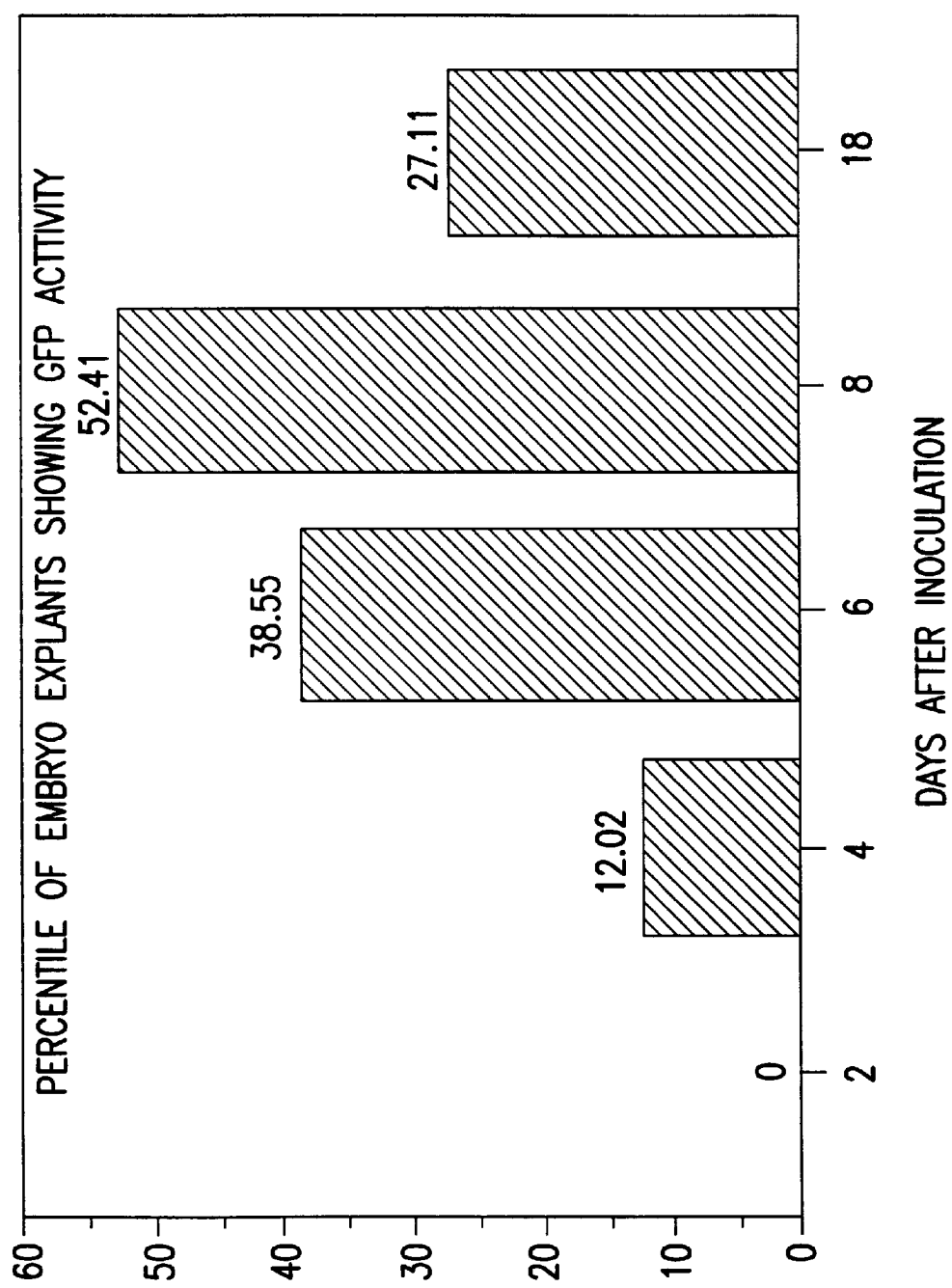
FIG. 13 is a graph representing transient GFP expression in somatic embryos of cacao genotype Sca-6 after Agrobacterium-mediated transformation.

After co-cultivation with Agrobacterium on ED medium, all of the inoculated embryos were transferred into a sterile 50-ml centrifuge tube containing 40 ml of sterile water. The tube was inverted several times to wash out attached bacteria from the surface of the embryos. The supernatant was removed completely. Forty ml of sterile water containing 400 mg/l Claforan was added to the tube. The washing process was repeated and the aqueous solution was removed. The embryos were placed briefly on the surface of a sterile paper towel to remove excessive water. The embryos were transferred onto a Petri dish containing 30 ml of PS medium. The dishes were sealed and cultured at 25° C. in the dark for 4 days. During this period of primary selection on solid medium, the presence of green fluorescence derived from the expression of GFP gene on the surface of inoculated embryos was monitored on a daily basis using a dissecting microscope equipped with an MVI fluorescence attachment. Tissues were illuminated with blue light and GFP emission was monitored using green baud pass FITC filters. The position of GFP-positive embryos was marked on the culture plate. Based on the transient gene expression studies, the GFP expression in inoculated cacao embryos became detectable 4 days after Agrobacterium infection (FIG. 13). Since then, the GFP expression frequency gradually increased, up to the 8th day, and then started to decline. Accordingly, inoculated embryos can be monitored for GFP expression for more than 6 days after infection, provided that the bacteria do not overgrow on the surface of the embryo tissue. In this way, more GFP-positive embryos may be identified and used in the subsequent selection process.

About 20 GFP-positive embryos were transferred into a sterile flask containing 30 ml of SS medium. The flasks were covered and sealed with parafilm. Cultures were maintained on a gyratory shaker at 100 rpm under dim light. Embryos were subcultured to fresh medium every 10 days. During this selection period, the cell division activity of the GFP-expressing foci was inspected regularly to identify the formation of GFP-positive microcalli on the surface of inoculated embryos. GFP-positive microcalli were excised and transferred to Petri dishes containing 30 ml of SS medium solidified with 2.0 g/l phytagel. The calli were cultured in the dark at 25±2° C. with a subculture interval of 14 days.

GFP-positive calli about 3 mm in size were transferred and cultured on solid SS medium modified to contain 100 mg/l Claforan and 50 mg/l kanamycin. Secondary embryos produced from the transformed GFP-positive callus tissue were transferred to Petri dishes containing 30 ml of ED medium. Transgenic plantlets were recovered by following the culture steps for somatic embryo maturation and plant regeneration described in Examples 1 and 2.

Experimental Results

Figure 9:
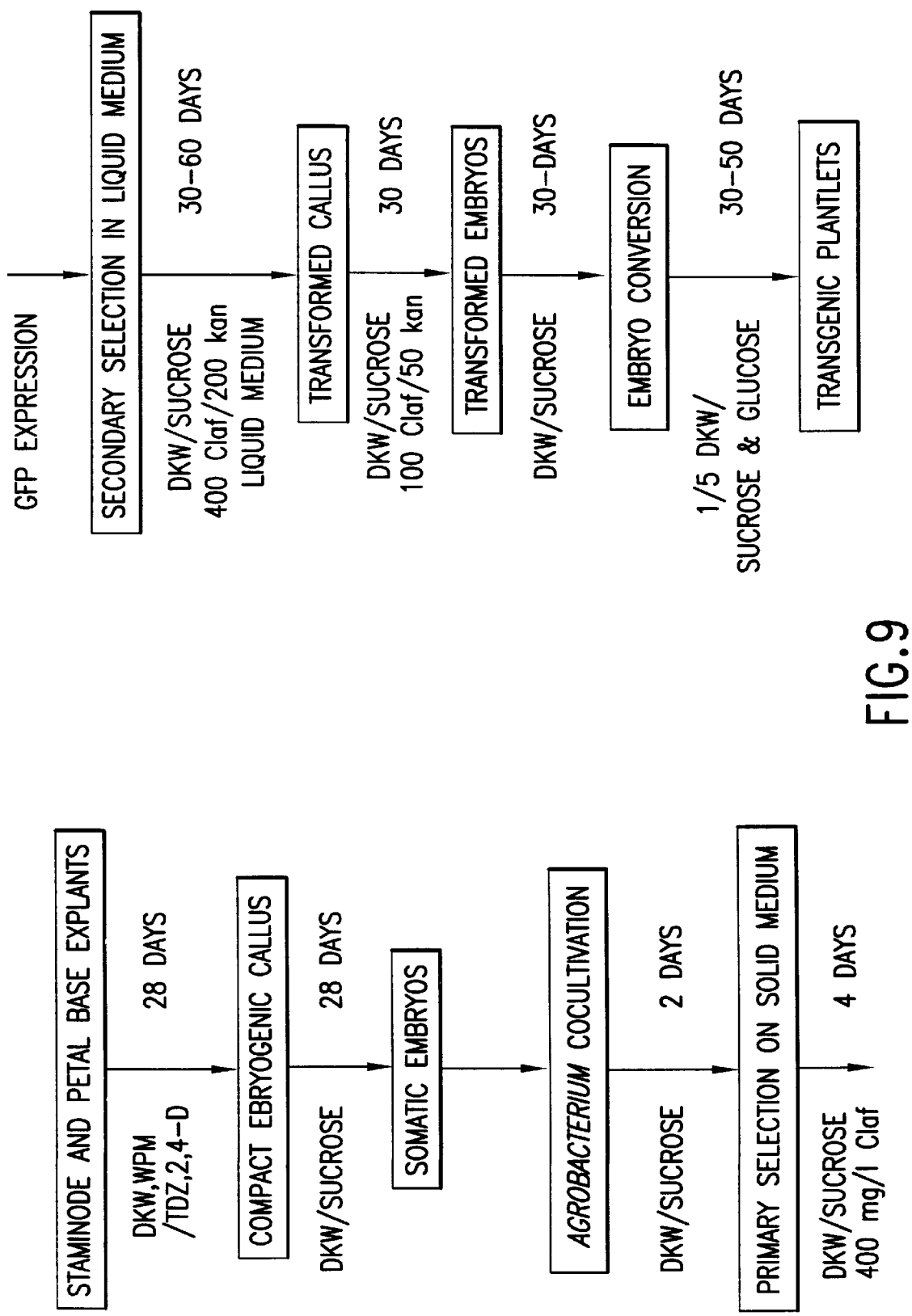
FIG. 9 is a schematic outline of the procedure for Agrobacterium-mediated transformation of cacao according to one aspect of the invention.
Figure 10:
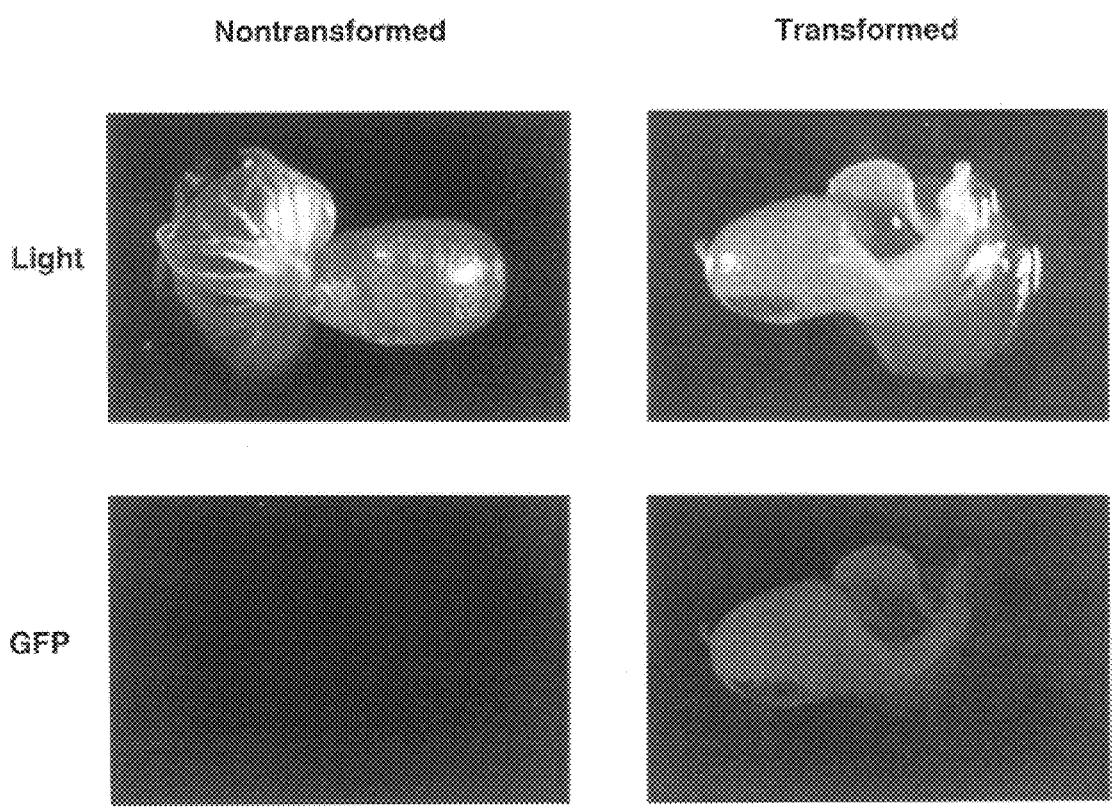
FIG. 10 is a photograph representing the expression of GFP in putative transgenic somatic embryos of cacao after Agrobacterium-mediated transformation.

The procedure used in this example for Agrobacterium-mediated transformation of cacao somatic embryos is outlined schematically in FIG. 9. The expression of GFP in putative transgenic somatic embryos of cacao after Agrobacterium-mediated transformation was measured and is shown in FIG. 10.

Figure 12:
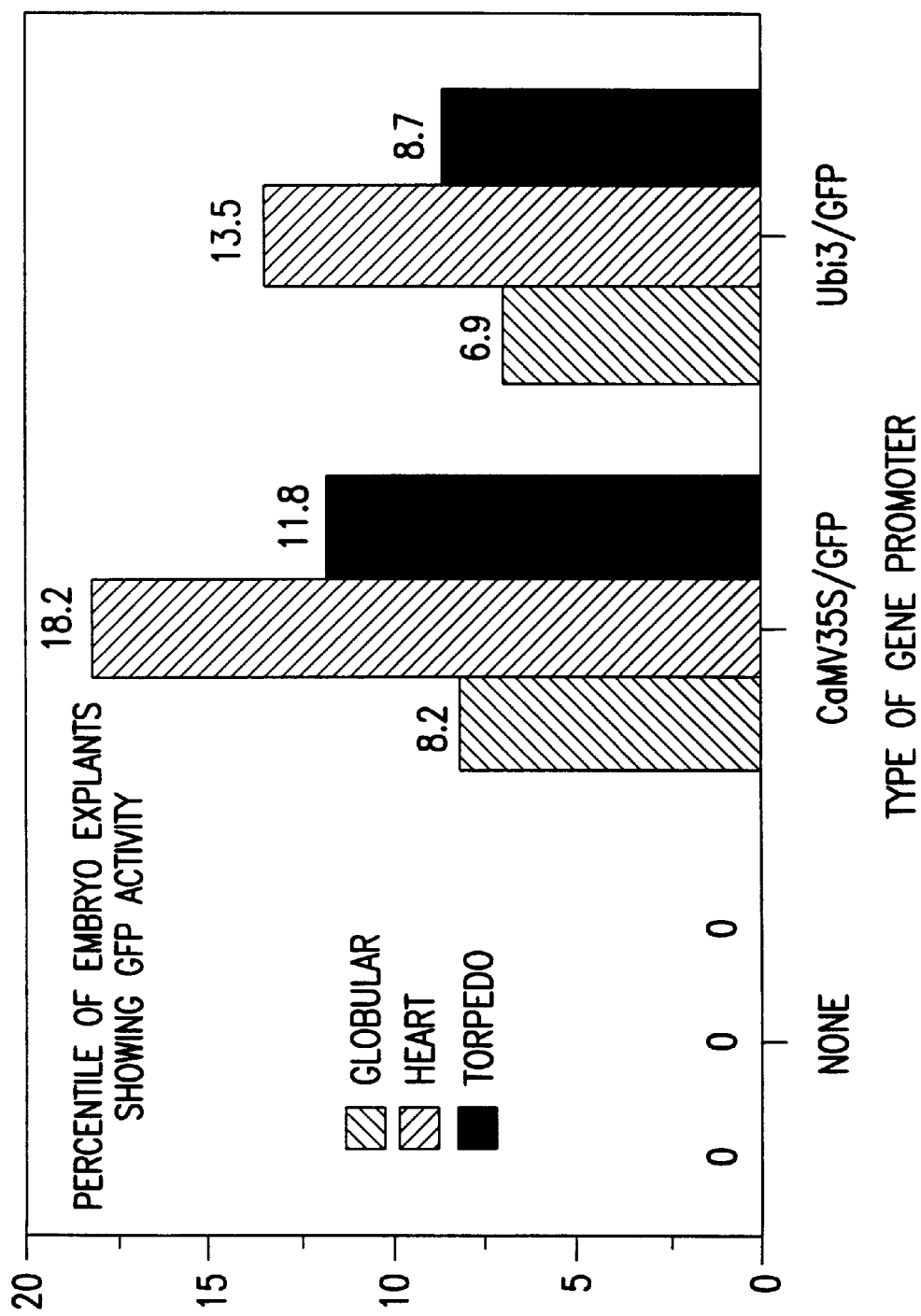
FIG. 12 is a graph showing the effect of developmental stages of cacao somatic embryos and gene promoters on transient GFP expression after Agrobacterium-mediated transformation.

The effects of developmental stages of cacao somatic embryos and gene promoters on transient GFP expression after Agrobacterium-mediated transformation were determined and are shown in FIG. 12. Somatic embryos of cacao genotype Sca-6 at various developmental stages were inoculated with *A. tumefaciens* strain EH101 carrying binary plasmids of either pDM96.0501 or pDU96.4451. Inoculated embryos were cultured on ED medium containing Claforan and monitored for GFP expression. Data were collected 10 days after infection. The values shown in FIG. 12 represent the percentile of globular-, heart-, and torpedo-shaped embryo explants with either the CaMV35S/GFP or Ubi3/GFP promoter which showed GFP activity.

The transient GFP expression in somatic embryos of cacao genotype Sca-6 after Agrobacterium-mediated transformation was monitored and the results are shown in FIG. 13. Somatic embryos at the heart-shaped developmental stage were infected with pretreated *A. tumefaciens* strain EHA101 carrying a binary plasmid pDM96.0501 and subsequently subjected to culture on ED medium containing Claforan. GFP expression in inoculated embryos was monitored daily. Data were averaged from three replica plates, each containing about 40 embryos. Bar values represent the percentile of embryo explants which showed GFP activity 2, 4, 6, 8, or 18 days after inoculation.

What is claimed is:

1. A method of inducing somatic embryogenesis in a cacao tissue comprising the steps of:
   (a) providing a cacao tissue explant;
   (b) culturing the explant on a primary callus growth medium having the property of inducing callus growth on the explant, wherein the primary callus growth medium comprises a DKW basal medium, a carbon source, and a growth regulator selected from a cytokinin, an auxin or a combination thereof;
   (c) culturing the callus produced in step (b) on a secondary callus growth medium, having the property of inducing homeostatic growth and bipolar callus cell development, wherein the secondary callus growth medium comprises a WPM low salt basal medium, a carbon source, and a growth regulator selected from a cytokinin, an auxin or a combination thereof; and
   (d) culturing the callus produced in step (c) on an embryo development medium having the property of inducing embryo differentiation, wherein the embryo development medium comprises a DKW basal medium and a carbon source.

2. The method of claim 1 wherein the carbon source is glucose, sucrose, or a combination thereof, at a concentration of from about 10 to 40 g/l.

3. The method of claim 2 wherein the carbon source in the primary callus growth medium is glucose at a concentration of about 20 g/l.

4. The method of claim 2 wherein the carbon source in the secondary callus growth medium is glucose at a concentration of from about 20 to 30 g/l.

5. The method of claim 1 wherein the cytokinin in the primary callus growth medium is thidiazuron, and the auxin is 2,4-dichlorophenoxyacetic acid.

6. The method of claim 5 wherein the growth regulator is a combination of thidiazuron at a concentration of from about 5 to 10 µg/l and 2,4-dichlorophenoxyacetic acid at a concentration of from about 1.5 to 2 mg/l.

7. The method of claim 1 wherein the cytokinin in the secondary callus growth medium is kinetin or 6-benzyladenine, and the auxin is 2,4-dichlorophenoxyacetic acid.

8. The method of claim 7 wherein the growth regulator is a combination of kinetin at a concentration of from about 0.1 to 0.5 mg/l and 2,4-dichlorophenoxyacetic acid at a concentration of from about 0.9 to 2 mg/l.

9. The method of claim 1 wherein said explant is a staminode or a petal base explant.

10. A method for regenerating cacao plantlets comprising the steps of:
    (a) providing a cacao somatic embryo produced according to claim 1;
    (b) germinating the somatic embryo of step (a) on a primary embryo conversion medium comprising a DKW basal medium, $KNO_3$, and a carbon source; and
    (c) regenerating a cacao plantlet from the germinated embryo produced in step (b) on a secondary embryo conversion medium comprising a diluted basal medium, a source of potassium and nitrogen, and a carbon source.

11. The method of claim 10 wherein the carbon source in the primary embryo conversion medium and the secondary embryo conversion medium is sucrose, glucose, or a combination thereof, at a concentration of from about 1 to 30 g/l.

12. A method for regenerating cacao plantlets comprising the steps of:
    (a) providing a cacao somatic embryo produced according to claim 1;
    (b) culturing the somatic embryo of step (a) on a plant regeneration medium comprising a diluted DKW basal medium and a carbon source.

13. The method of claim 12 wherein the carbon source in the plant regeneration medium is glucose, sucrose, or a combination thereof, at a concentration of from about 1 to 20 g/l.

14. The method of claim 12 wherein the plant regeneration medium further comprises a growth hormone.

15. The method of claim 14 wherein the growth hormone in the plant regeneration medium is gibberellic acid.

16. The method of claim 15 wherein the gibberellic acid is at a concentration of from about 0.1 to 3 mg/l.

* * * * *